US008283936B2

(12) United States Patent  
Iqbal et al.

(10) Patent No.: US 8,283,936 B2  
(45) Date of Patent: Oct. 9, 2012

(54) NANO-SCALE BIOSENSORS

(75) Inventors: Samir M. Iqbal, Irving, TX (US); Swati Goyal, Arlington, TX (US); Shawn M. Christensen, Arlington, TX (US); Mohammud R. Noor, Arlington, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 431 days.

(21) Appl. No.: 12/701,888

(22) Filed: Feb. 8, 2010

(65) Prior Publication Data

US 2010/0201381 A1    Aug. 12, 2010

Related U.S. Application Data

(60) Provisional application No. 61/150,976, filed on Feb. 9, 2009.

(51) Int. Cl.  
*G01R 27/26* (2006.01)  
*G01R 27/08* (2006.01)

(52) U.S. Cl. .................... 324/663; 324/693; 977/953

(58) Field of Classification Search .............. 324/663, 324/658, 649, 600, 693, 691, 71.1, 76.11, 324/692; 977/957, 953, 932, 902; 702/1, 702/19, 127  
See application file for complete search history.

(56) References Cited

U.S. PATENT DOCUMENTS

| | | | |
|---|---|---|---|
| 6,465,175 B2 * | 10/2002 | Horn et al. .................... 435/6.12 |
| 2004/0191801 A1 | 9/2004 | Heeger et al. | |
| 2006/0134657 A1 | 6/2006 | Hodko et al. | |
| 2007/0178477 A1 | 8/2007 | Joiner, Jr. et al. | |
| 2010/0184062 A1 * | 7/2010 | Steinmuller-Nethl et al. ... 435/6 |
| 2011/0056845 A1 * | 3/2011 | Stellacci et al. ........... 205/777.5 |
| 2011/0287956 A1 * | 11/2011 | Iqbal et al. ........................ 506/9 |

FOREIGN PATENT DOCUMENTS

CN    101078026 A    11/2007

OTHER PUBLICATIONS

Aerts, Wouter F. et al., "Design of an Organic Pixel Addressing Circuit for an Active-Matrix OLED Display", IEEE Transactions on Electron Devices Dec. 2002, vol. 49, No. 12, 2124-2130.

Ahmadi, Temer S. et al., "Shape-Controlled Synthesis of Colloidal Platinum Nanoparticles", Science Jun. 28, 1996, vol. 22; 1924-1926.

Allara, David L. et al., "Spontaneously Organized Molecular Assemblies. 1. Formation, Dynamics, and Physical Properties of n-Alkanoic Acids Adsorbed from Solution on an Oxidized Aluminum Surface", Langmuir 1985, 1:45-52.

Ashgar, Waseem et al., "Rapid Nanomanufacturing of Metallic Break Junctions Using Focused Ion Beam Scratching and Electromigration", Doctoral Thesis Jan. 14, 2010.

(Continued)

*Primary Examiner* — Hoai-An D Nguyen  
(74) *Attorney, Agent, or Firm* — Kilpatrick Townsend & Stockton LLP

(57) ABSTRACT

Devices, systems, and methods for detecting nucleic acid hybridization, including single nucleic base mutations at low concentrations, are disclosed, using surface-tethered hairpin loop oligonucleotide probes and metal-nanoparticles conjugated to a hybridization detection sequence that is capable of binding the stem region of the opened hairpin loop oligonucleotide probe, without the use of labeling or target modification and capable of recycling.

42 Claims, 18 Drawing Sheets

OTHER PUBLICATIONS

Bahnemann, D. W. "Mechanisms of Organic Transformations on Semiconductor Particles", Photochemical Converstion and Storage of Solar Energy 1991, 251-276.

Beaucage, S.L. et al., "Deoxynucleoside Phosphoramidites—A New Class of Key Intermediates for Deoxypolynucleotide Synthesis", Tetrahedron Letters 1981, vol. 22, No. 20, pp. 1859-1862.

Bezryadin, A. et al., "Electrostatic trapping of single conducting nanoparticles between nanoelectrodes", Appl. Phys. Lett. Sep. 1, 1997, 71(9): 1273-1275.

Bezryadin, A. et al., "Nanofabrication of electrodes with sub-5 nm spacing for transport experiments on single molecules and metal clusters", J. Vac. Sci. Technol. Jul./Aug. 1997, 15(4): 793-799.

Braun, Erez et al., "DNA-templated assembly and electrode attachment of a conducting silver wire", Nature Feb. 19, 1998, vol. 391, 775-778.

Braun, Erez et al., "DNA-templated assembly and electrode attachment of a conducting silver wire", Nature Feb. 19, 1998, vol. 391; 775-778.

Brus, L. "Quantum Crystallites and Nonlinear Optics", Appl. Phys. Sep. 27, 199 , A53: 465-474.

Burwell, Robert L. "Modified silica gels as adsorbents and catalysts", Chemtech Jun. 1974, 370-377.

Cagnin, Stefano et al., "Overview of Electrochemical DNA Biosensors: New Approaches to Detect the Expression of Life", Sensors 2009, 9, 3122-3148.

Christensen, Shawn M. et al., "Role of the Bombyx mori R2 element N-terminal domain in the target-primed reverse transcription (TPRT) reaction", Nucleic Acids Research Nov. 10, 2005, vol. 33, No. 20, 6461-6468.

Curtis, Andrew C. et al., "A Morphology-Selective Copper Organosol", Angew. Chem. Int. Ed. Engl. 1988, vol. 27, No. 11, pp. 1530-1533.

Eltekova, Nina A. et al., "Adsorption of Aromatic Compounds from Solutions on Titanium Dioxide and Silica", Langmuir 1987, 3: 951-957.

Gadgil, V.J. et al., "Fabrication of nano structures in thin membranes with focused ion beam technology", Surface & Coatings Technology 2009, 203: 2436-2441.

Goyal, Swati "Nanoscale Approaches for Biomolecule Separation and Detection", Doctoral Thesis Dec. 2009.

Grabar, Katherine C. et al., "Preparation and Characterization of Au Colloid Monolayers", Analytical Chemistry Feb. 15, 1995, vol. 67, No. 4, 735-473.

Hassibi, Arjang et al., "A Programmable 0.18-um CMOS Electrochemical Sensor Microarray for Biomolecular Detection", IEEE Sensors Journal Dec. 2006, vol. 6, No. 6, 1380-1388.

Hassibi, Arjang "Integrated Microarrays", Doctoral Thesis Jun. 2005.

Henglein, A. et al., "Absorption Sectrum and Some Chemical Reactions of Colloidal Platinum in Aqueous Solution", J. Phys. Chem. 1995, 99: 14129-14136.

Henglein, Arnim "Mechanism of Reactions on Colloidal Microelectrodes and Size Quantization Effects", Topics in Current Chemistry 1988, vol. 143; pp. 113-180.

Henglin, Arnim "Small-Particle Research: Physicochemical Properties of Extremely Small Colloidal Metal and Semiconductor Particles", Chem. Rev. 1989, 89: 1861-1873.

Hickman, James J. et al., "Combining Spontaneous Molecular Assembly with Microfabrication to Pattern Surfaces: Selective Binding of Isonitriles to Platinum Microwires and Characterization by Electrochemistry and Surface Spectroscopy", J. Am. Chem. Soc. 1989, 111: 7271-7272.

Hubbard, Arthur T. "Electrochemistry of Well-Defined Surfaces", Acc. Chem. Res. 1980, 13: 177-184.

Huncharek, Michael et al., "K-ras oncogene mutation as a prognostic marker in non-small cell lung cancer: a combined analysis of 881 cases", Carcinogenesis 1999, vol. 20, No. 8, pp. 1507-1510.

Iler, "The Surface Chemistry of Silica", The Chemistry of Silica 1979, Chapter 6: 622-729.

Iqbal, Samir M. "An electrical framework for detection and characterization of DNA using nanoscale silicon based sensors", Doctoral Dissertations, Purdue e-Pubs Jan. 1, 2007.

Iqbal, Samir M. "An Electrical Framework for Detection and Characterization of DNA Using Nanoscale Silicon Based Sensors", Thesis May 2007, 1-211.

Iqbal, Samir M. et al., "Direct current electrical characterization of ds-DNA in nanogap junctions", Applied Physics Letters 2005, 86: 153901.

Iqbal, Samir M. et al., "Solid-state nanopore channels with DNA selectivity", nature nanotechnology Apr. 1, 2007, doi: 10.1038/nnano.2007.78: 1-6.

Iqbal, Samir M. et al., "Title of Project: Ultrasensitive and Label-Free Solid-state Nanoarray Chips for Gene Expression", Application No. AN:3060783, Supplemental Update.

Jain, A. et al., "Investigation of Temperature Gradient Effects on Neurite Outgrowth in Nerve Cells Using a Microfabricated Heater Structure", Proceedings of the 3rd Annual International IEEE EMBS Special Topic; Conference on Microtechnologies in Medicine and Biology; Kahuku, Oahu, Hawaii May 12-15, 2005.

Lee, Haiwon et al., "Adsorption of Ordered Zirconium Phosphonate Multilayer Films on Silicon and Gold Surfaces", J. Phys. Chem. 1988, 92: 2597-2601.

Mahapatro, Ajit K. et al., "Nanometer Scale Electrode Separation (Nanogap) Using Electromigration at Room Temperature", IEEE Transactions on Nanotechnology May 2006, vol. 5, No. 3, 232-236.

Manning, M et al., "A versatile multi-platform biochip surface attachment chemistry", Materials Science and Engineering 2003, 23: 347-351.

Maoz, Rivka et al., "Penetration-Controlled Reactions in Organized Monolayer Assemblies. 2. Aqueous Permanganate Interaction with Self-Assembline Monolayers of Long-Chain Surfactants", Langmuir 1987, 3: 1045-1051.

Maoz, Rivka et al., "Penetration-Controlled Reactions in Organized Monolayer Assemblies. 2. Aqueous Permanganate Interaction with Self-Assembling Monolayers of Long-Chain Surfactants", Langmuir 1987, 3: 1045-1051.

Massart, Rene "Preparation of Aqueous Magnetic Liquids in Alkaline and Acidic Media", IEEE Transactions on Magnetics Mar. 1981, vol. Mag-17, No. 2, pp. 1247-1248.

Matteucci, M. D. et al., "Synthesis of Deoxyoligonucleotides on a Polymer Support", J. Am. Chem. Soc. 1981, 103: 3185-3191.

Mucic, Robert C. et al., "Synthesis and characterization of DNA with ferrocenyl groups attached to their 5'termini: electrochemical characterization of a redox-active nucleotide monolayer", Chem. Commun. 1996, 555-557.

Noor, Muhammud R. "Electrical detection of single-base DNA mutation using functionalized nanoparticles", Thesis Dec. 2009, 1-90.

Noor, Mohammud R. et al., "Electrical detection of single-base DNA mutation using functionalized nanoparticles", Applied Physics Letters 2009, 95, 073703, pp. 1-3.

Nuzzo, Ralph G. et al., "Spontaneously Organized Molecular Assemblies. 3. Preparation and Properties of Solution Adsorbed Monolayers of Organic Disulfides on Gold Surfaces", J. Am. Chem. Soc. 1987, 109: 2358-2368.

Olshavsky, M. A. et al., "Organometallic Synthesis of GaAs Crystallites Exhibiting Quantum Confinement", J. Am. Chem. Soc. 1990, 112: 9438-9439.

Park, Jiwoong et al., "Coulomb blockade and the Kondo effect in single atom transistors", Nature 2002, 417(6890): 722-725.

Park, Hongkun et al., "Fabrication of metallic electrodes with nanometer separation of electromigration", Applied Physics Letters Jul. 12, 1999, vol. 75, No. 2, 301-303.

Rakitin, A et al., "Metallic conduction through engineered DNA: DNA nanoelectronic building blocks.", Phys Rev Lett Apr. 16, 2001, 86(16):3670-3.

Ramachandran, Priyanka P. et al., "Electronic Detection of Selective Proteins using Non Antibody-Based CMOS Chip", IEEE/NIH Life Science Systems and Applications Workshop 2009, 1-4.

Simmons, John G. et al., "Generalized Formula for the Electric Tunnel Effect between Similar Electrodes Separated by a Thin Insulating Film", Journal of Applied Physics Jun. 1963, vol. 34, No. 6, 1793-1803.

Soriaga, Manuel P. et al., "Determination of the Orientation of Aromatic Molecules Adsorbed on Platinum Electrodes. The Effect of Solute Concentration", J. Am. Chem. Soc. 1982, 104: 3937-3945.

Storhoff, James J. et al., "One-Pot Colorimetric Differentiation of Polynucleotides with Single Base Imperfections Using Gold Nanoparticle Probes", J. Am. Chem. Soc. 1998, 120: 1595-1064.

Strachan, D. R. et al., "Controlled Fabrication of Nanogaps in Ambient Environment for Molecular Electronics", arXiv:cond-mat/0504112v1 [cond-mat.mes-hall] Apr. 5, 2005, 1-3.

Timmons, C. O. et al., "Investigation of Fatty Acid Monolayers on Metals by Contact", The Journal of Physical Chemistry Mar. 1965, vol. 69, No. 8, 984-990.

Tompkins, Harland G. et al., "The Study of the Gas-Solid Interaction of Acetic Acid with a Cuprous Oxide Surface Using Reflection-Absorption Spectroscopy", Journal of Colloid and Interface Science Dec. 1974, vol. 49, No. 3, 410-421.

Uchida, Hiroyki et al., "GaAs Nanocrystals Prepared in Quinoline", The Journal of Physical Chemistry 1991, vol. 95, No. 14, 582-584.

Wang, Y. et al., "Nanometer-Sized Semiconductor Clusters: Materials Synthesis, Quantum Size Effects, and Photophysical Properties", J. Phys. Chem. 1991, 95: 525-532.

Wasserman, Stephen R. et al., "Structure and Reactivity of Alkylsiloxane Monolayers Formed by Reaction of Alkyltrichlorosilanes on Silicon Substrates", Langmuir 1989, 5: 1074-1087.

Weller, Horst "Colloidal Semiconductor Q-Particles: Chemistry in the Transition Region Between Solid State and Molecules", Angew. Chem. Int. Ed. Engl. 1993, 32: 41-53.

Whitesides, George M. et al., "Self-Assembled Monolayers and Lithography", Proceedings of the Robert A. Welch Foundation 39th Conference on Chemical Research Nanophase Chemistry, Houston TX 1995, 109-121.

Zhou, C. et al., "Microfabrication of a mechanically controllable break junction in silicon", Appl. Phys. Lett. Aug. 21, 1995, 67 (8): 1160-1162.

\* cited by examiner

FIGURE 4A
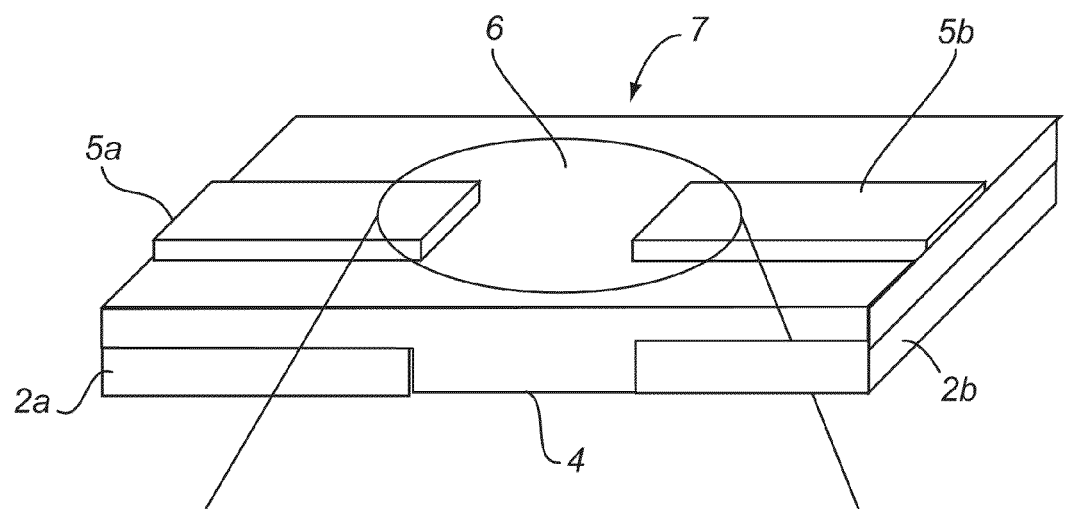
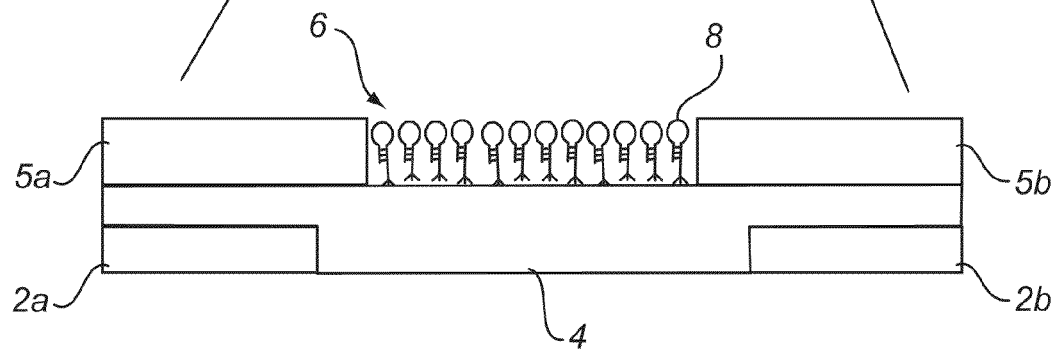
FIGURE 4B

NANO-SCALE BIOSENSORS

CROSS REFERENCE TO RELATED APPLICATIONS

This application claims the benefit of U.S. Application No. 61/150,976, filed Feb. 9, 2009, the disclosure of which is incorporated herein by reference in its entirety.

REFERENCE TO GOVERNMENT GRANTS

Portions of the disclosure herein may have been supported, in part, by a grant from the National Science Foundation (CAREER Grant No. ECCS 0845669). The United States Government may have certain rights in this application.

FIELD OF THE INVENTION

The invention relates generally to devices, systems, and methods for detecting nucleic acid hybridization, including single nucleic base mutations, are disclosed, using surface-tethered hairpin loop oligonucleotide probes and metal-nanoparticles conjugated to a hybridization detection sequence that is capable of binding the stem of region of the opened hairpin loop oligonucleotide probe, without the use of labeling or target modification.

BACKGROUND OF THE INVENTION

Individual genetic mutations can predispose a cell or tissue toward certain diseases, such as most cancers, cystic fibrosis, and sickle cell anemia. Specific mutations in such genes can thus be used as diagnostic indicators for the susceptibility of disease, aiding in early detection and treatment. The high-throughput detection of genes has been studied for several years and devices like microarrays and the DNA chip have significantly increased our capabilities.

The basic principle of microarray technology requires tagging of the sample with fluorescent dyes. However, these modifications can change the thermodynamic properties of the molecular interactions of DNA and, in some cases, unnaturally stabilize or destabilize the DNA double-strand and change the melting temperature significantly. Additionally, expensive fluorescent microscopes are needed to visualize the data and normalization of the data to references remain problematic. Further, the hybridization of the probe and target molecules is a diffusion-limited process requiring long-incubation times as the target molecules must travel to the arrayed probes on the surface of the chip. The fluorophores are also known to have great effect on the stability of the duplexes as a function of the sequence itself. In addition, fluorescent dyes photobleach, quench statically, or interact with each other, so the microarray technologists need to have very detailed knowledge about the limitations of the optics, reagents used, and the sample interactions.

Several silicon-based approaches have been reported for chemical and biological sensing. While many of the silicon-based sensors can be fabricated with compact size, none of these efforts have resulted in a portable sensor with adequate performance. The hybridization of DNA with probe-functionalized chip surfaces has been studied for biophysical characterization and kinetics studies but its use in a functional nano-scale device has not been reported. The challenges range from the costly and lengthy fabrication processes to the need for external expensive measurement equipment. The DNA hybridization detection techniques have been implemented on chips but throughput, cost, and multiplexing have not been adequately addressed.

The solid-state DNA interaction detection techniques have also required tagging of target with electrical markers, resulting in possibly altered interactions while requiring sample preparation. The DNA electrical detection techniques mostly employ electrochemical impedance spectroscopy, capillary electrophoresis, or charge perturbation detection using labeled target or labeled probe molecules, surface attached antibodies, and/or with pre-/post-PCR. In label-free detection schemes, the probe DNA is immobilized on the electrodes and impedance is measured in conjunction with or without a reference electrode.

Thus, there is a need for biosensors that overcome these problems The invention is directed to these, as well as other, important ends.

SUMMARY OF THE INVENTION

The invention provides a nanotechnology-based low-power, rapid, inexpensive, recyclable, and sensitive electrical detection device, system, and method of sub-femtomolar concentrations of nucleic acids, including genes, with no external sample preparation or labeling or other chemical modification of the sample. The biosensors of the invention may be used in wide variety of applications requiring sensitive nucleic acid detection, including, but not limited to, forensics, early disease detection, disease progression monitoring (such as in response to therapy and/or medicinal agents), legal matters (such as paternity and criminal proceedings), defensive biohazard detection, and immigration issues (such as establishing blood relationships). The biosensors of the invention are useful in further enabling "personalized medicine," where drugs are designed according to each individual's genetic make-up.

The invention involves a number of features:
- use of nanoimprint lithography-based techniques to make chips with arrays of nanogap electrodes and embedded heaters for on-chip sample treatment, for recycling of the chip for next batch of targets, and for temperature gradient focusing of the target nucleic acids;
- use of surface bound hairpin loop nucleic acid probes that are capable of distinguishing between solution phase perfect complementary and single-base mismatched sequences;
- use of a nanoparticle conjugated to a short sequence of nucleic acids as a detector to quantify the level of hybridization between probe and target DNA molecules; and
- use of low-power printed circuit board electronics to interrogate the mass fabricated interaction sites and electrical sensing of the nucleic acid hybridization.

In one embodiment, the invention is directed to devices, comprise:
a thermally responsive, electrically insulating substrate;
at least one heating element; and
a first detecting unit, comprising:
a first electrode and a second electrode separated by a nanogap; and
a plurality of first oligonucleotide probes attached to said substrate in said nanogap;
wherein said first oligonucleotide probes are in a hairpin loop formation and have the same nucleic acid sequence; and
wherein said first oligonucleotide probes comprise an optional spacer, a loop, and a stem region, said stem region being double-stranded.

In another embodiment, the invention is directed to devices described herein, further comprising:
a plurality of second detecting units, comprising:
a first electrode and a second electrode separated by a nanogap; and
a plurality of second oligonucleotide probes attached to said substrate in said nanogap;
wherein said second oligonucleotide probes are in a hairpin loop formation and have the same nucleic acid sequence; and
wherein said second oligonucleotide probes comprise an optional spacer, a loop, and a stem region, said stem region being double-stranded;
wherein said second oligonucleotide probes are the same or different from said first oligonucleotide probes in said first detecting unit; and
wherein said second oligonucleotide probes are the same or different from other second oligonucleotide probes in said plurality of second detecting units.

In further embodiment, the invention is directed to devices described herein, further comprising:
a plurality of microfluidic channels; and
an optional cover.

In yet other embodiment, the invention is directed to systems, comprising:
a device described herein; and
a plurality of nanoparticle reporter conjugates;
wherein said nanoparticle reporter conjugates comprise at least one nanoparticle and a single-stranded oligonucleotide complementary to at least a portion of said stem of said first oligonucleotide probe.

In yet another embodiment, the invention is directed to systems, comprising:
a multiplexing device described herein; and
a plurality of first nanoparticle reporter conjugates; and
a plurality of at least one second nanoparticle reporter conjugates;
wherein said first nanoparticle reporter conjugates comprise at least one nanoparticle and a single-stranded oligonucleotide complementary to at least a portion of said stem of said first oligonucleotide probes;
wherein said nanoparticle in said first nanoparticle reporter conjugate is a metal, semiconductor, or magnetic colloidal particle;
wherein said second nanoparticle reporter conjugates comprise at least one nanoparticle and a single-stranded oligonucleotide complementary to at least a portion of said stem of said second oligonucleotide probes;
wherein said nanoparticle in said second nanoparticle reporter conjugate is a metal, semiconductor, or magnetic colloidal particle;
wherein said second nanoparticle reporter conjugates are the same or different from said first nanoparticle reporter conjugates; and
wherein said second nanoparticle reporter conjugates are the same or different from said other second nanoparticle reporter conjugates.

In other embodiments, the invention is directed to systems, further comprising:
an electrical reading device for interrogating said device described herein.

In one embodiment, the invention is directed to methods for detecting nucleic acid hybridization, comprising:
providing a device, comprising:
a thermally responsive, electrically insulating substrate;
at least one heating element; and
a first detecting unit, comprising:
a first electrode and a second electrode separated by a nanogap; and
a plurality of first oligonucleotide probes attached to said substrate in said nanogap;
wherein said first oligonucleotide probes are in a hairpin loop formation and have the same nucleic acid sequence; and
wherein said first oligonucleotide probes comprise an optional spacer, a loop, and a stem region, said stem region being double-stranded;
providing a solution comprising at least one buffer and single-stranded oligonucleotide target under hybridizing conditions;
wherein said single-stranded oligonucleotide target hybridizes at least some of said oligonucleotide probes to form elongated oligonucleotide probes;
providing a plurality of first nanoparticle reporter conjugates under hybridizing conditions;
wherein said first nanoparticle reporter conjugates comprise at least one nanoparticle and an oligonucleotide complementary to at least a portion of said stem of said first oligonucleotide probes;
wherein said nanoparticle in said first nanoparticle reporter conjugate is a metal, semiconductor, or magnetic colloidal particle;
applying a voltage drop across said electrodes; and
measuring a change in conductivity, resistivity, capacitance, or impedance across said electrodes at known locations to determine perfect complementarity of said oligonucleotide target to said first oligonucleotide probes.

In yet other embodiment, the invention is directed to methods further comprising:
washing to remove unhybridized components from said detecting unit.

In another embodiment, the invention is directed to methods further comprising:
heating said device to remove said hybridized targets and said hybridized nanoparticle reporter conjugates from said probe to permit recycling of said detecting unit.

In still further embodiments, the invention is directed to methods further comprising:
heating a solution comprising double stranded oligonucleotide target to form said solution comprising single-stranded oligonucleotide target.

In a further embodiment, the invention is directed to methods further comprising:
forming a temperature gradient to focus said single stranded oligonucleotide target at said detecting unit.

In one embodiment, the invention is directed to methods further comprising:
reversing the polarity of said voltage drop to remove unbound components or nonspecifically bound components from said detecting unit.

In another embodiment, the invention is directed to methods further comprising:
providing, in addition to said first detecting unit, a plurality of additional detecting units, each additional detecting unit comprising:
a first electrode and a second electrode separated by a nanogap; and
a plurality of second oligonucleotide probes attached to said substrate in said nanogap;
wherein said second oligonucleotide probes are in a hairpin loop formation and have the same nucleic acid sequence; and wherein said second oligonucleotide probes comprise an optional spacer, a loop, and a stem region, said stem region being double-stranded;

wherein said second oligonucleotide probes are the same or different from said first oligonucleotides in said first detecting unit; and wherein said second oligonucleotide probes are the same or different from other second oligonucleotide probes in said plurality of second detecting units;

providing a plurality of at least one second nanoparticle reporter conjugates under hybridizing conditions;

wherein said second nanoparticle reporter conjugates comprise at least one nanoparticle and an oligonucleotide complementary to at least a portion of said stem of said second oligonucleotide probes;

wherein said nanoparticle in said first nanoparticle reporter conjugate is a metal, semiconductor, or magnetic colloidal particle;

wherein said second nanoparticle reporter conjugates are the same or different from said first nanoparticle reporter conjugates;

wherein said second nanoparticle reporter conjugates are the same or different from said other second nanoparticle reporter conjugates;

wherein said measuring step is carried out in parallel or sequentially for said first detecting unit and said plurality of said additional detecting units.

In certain embodiments, the invention is directed to methods for detecting nucleic acid hybridization, comprising:
providing a device, comprising:
a thermally responsive, electrically insulating substrate;
at least one heating element; and
a first detecting unit, comprising:
a first electrode and a second electrode separated by a nanogap; and
a plurality of first oligonucleotide probes attached to said substrate in said nanogap;
wherein said first oligonucleotide probes are in a hairpin loop formation and have the same nucleic acid sequence; and
wherein said first oligonucleotide probes comprise an optional spacer, a loop, and a stem region, said stem region being double-stranded;
providing a solution comprising at least one buffer and single-stranded oligonucleotide target under hybridizing conditions;
wherein said single-stranded oligonucleotide target hybridizes at least some of said oligonucleotide probes to form elongated oligonucleotide probes;
providing a plurality of first reporter conjugates under hybridizing conditions;
wherein said first reporter conjugates comprise an oligonucleotide complementary to at least a portion of said stem of said first oligonucleotide probes;
reversibly exchanging an imino proton in each base pair of said first reporter conjugate or said stem of said first oligonucleotide probes with a metal ion selected from the group consisting of gold ion, silver ion, platinum ion, and copper ion;
applying a voltage drop across said electrodes; and
measuring a change in conductivity, resistivity, capacitance, or impedance across said electrodes at known locations to determine perfect complementarity of said oligonucleotide target to said first oligonucleotide probes.

In certain embodiments, the invention is directed to methods for detecting nucleic acid hybridization, comprising:
providing a device, comprising:
a thermally responsive, electrically insulating substrate;
at least one heating element; and
a first detecting unit, comprising:
a first electrode and a second electrode separated by a nanogap; and
a plurality of first oligonucleotide probes attached to said substrate in said nanogap;
wherein said first oligonucleotide probes are in a hairpin loop formation and have the same nucleic acid sequence; and
wherein said first oligonucleotide probes comprise an optional spacer, a loop, and a stem region, said stem region being double-stranded;
providing a solution comprising at least one buffer and single-stranded oligonucleotide target under hybridizing conditions;
wherein said single-stranded oligonucleotide target hybridizes at least some of said oligonucleotide probes to form elongated oligonucleotide probes;
providing a plurality of first nanoparticle reporter conjugates under hybridizing conditions to form a double stranded nucleic acid sequence;
wherein said first nanoparticle reporter conjugates comprise an oligonucleotide complementary to at least a portion of said stem of said first oligonucleotide probes;
vectorially depositing silver on said double stranded nucleic acid sequence;
applying a voltage drop across said electrodes; and
measuring a change in conductivity, resistivity, capacitance, or impedance across said electrodes at known locations to determine perfect complementarity of said oligonucleotide target to said first oligonucleotide probes.

In certain embodiments, the invention is directed to methods for detecting nucleic acid hybridization, comprising:
providing a device, comprising:
a thermally responsive, electrically insulating substrate;
at least one heating element; and
a first detecting unit, comprising:
a first electrode and a second electrode separated by a nanogap; and
a plurality of first oligonucleotide probes attached to said substrate in said nanogap;
wherein said first oligonucleotide probes are in a hairpin loop formation and have the same nucleic acid sequence; and
wherein said first oligonucleotide probes comprise an optional spacer, a loop, and a stem region, said stem region being double-stranded;
providing a solution comprising at least one buffer and single-stranded oligonucleotide target under hybridizing conditions;
wherein said single-stranded oligonucleotide target hybridizes at least some of said first oligonucleotide probes to form elongated oligonucleotide probes;
providing a plurality of first reporter molecules under hybridizing conditions to form a double stranded oligonucleotide-stem complex;
wherein said first reporter molecules comprise an oligonucleotide complementary to at least a portion of said stem of said first oligonucleotide probes;
providing a solution comprising first nanoparticle polypeptide conjugates;
wherein said first nanoparticle polypeptide conjugates comprise at least one nanoparticle and a polypeptide that binds to said double stranded oligonucleotide-stem complex;

wherein said nanoparticle in said first nanoparticle polypeptide conjugates is a metal, semiconductor, or magnetic colloidal particle;

applying a voltage drop across said electrodes; and measuring a change in conductivity, resistivity, capacitance, or impedance across said electrodes at known locations to determine perfect complementarity of said oligonucleotide target to said first oligonucleotide probes.

In certain embodiments, the invention is directed to methods of forming a metallic nano-scale break junction on a chip, comprising:

forming on said chip a metal line, preferably having a thickness of less than about 5 μm and a width less than about 5 μm;

bombarding said metal line with a focused-ion beam to form a thinned section in said metal line; and applying current to said metal line sufficient to cause electromigration in said thinned section of said metal line.

In preferred embodiments, the metal line is formed using photolithography.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

FIG. 4A is a schematic view of metal nanoplates as heating elements 2a, 2b embedded on a silicon dioxide chip 1 with a set of electrodes 5a, 5b with a nanogap 6. FIG. 4B is an expanded side view of metal nanoplates as heating elements 2a, 2b embedded on a silicon dioxide chip 1 with a set of electrodes 5a, 5b with a nanogap 6 shown in FIG. 4A, but also showing the attached hairpin loop oligonucleotide probes 8.

FIG. 7A shows double-stranded oligonucleotide target molecules 10 present at the nanogap 6 of the electrodes 5a, 5b (heating elements 2a, 2b and hairpin loop oligonucleotide probes 8 also shown). FIG. 7B shows melting of the double-stranded oligonucleotide target molecules 10 to single-stranded oligonucleotide target molecules 11 present at the nanogap of the electrodes nanogap 6 of the electrodes 5a, 5b. FIG. 7C shows hybridization of the single-stranded oligonucleotide target molecules 10 present at the nanogap 6 of the electrodes nanogap 6 of the electrodes 5a, 5b to the oligonucleotide probes, causing the hairpin loop formation to open 13 and also exposing unhybridized nucleotide bases in the stem region of the oligonucleotide probes.

FIG. 8A shows when the device of the invention is exposed to mismatched target for the hairpin loop probes. FIG. 8B shows when the device of the invention is exposed to perfectly complementary target. FIG. 8C shows the details of FIG. 8B. These figures demonstrate the basic biochemical interactions on the surface of the silicon dioxide chips.

Chip 1: silane+gold nanoparticle reporter conjugate

Figure 10:
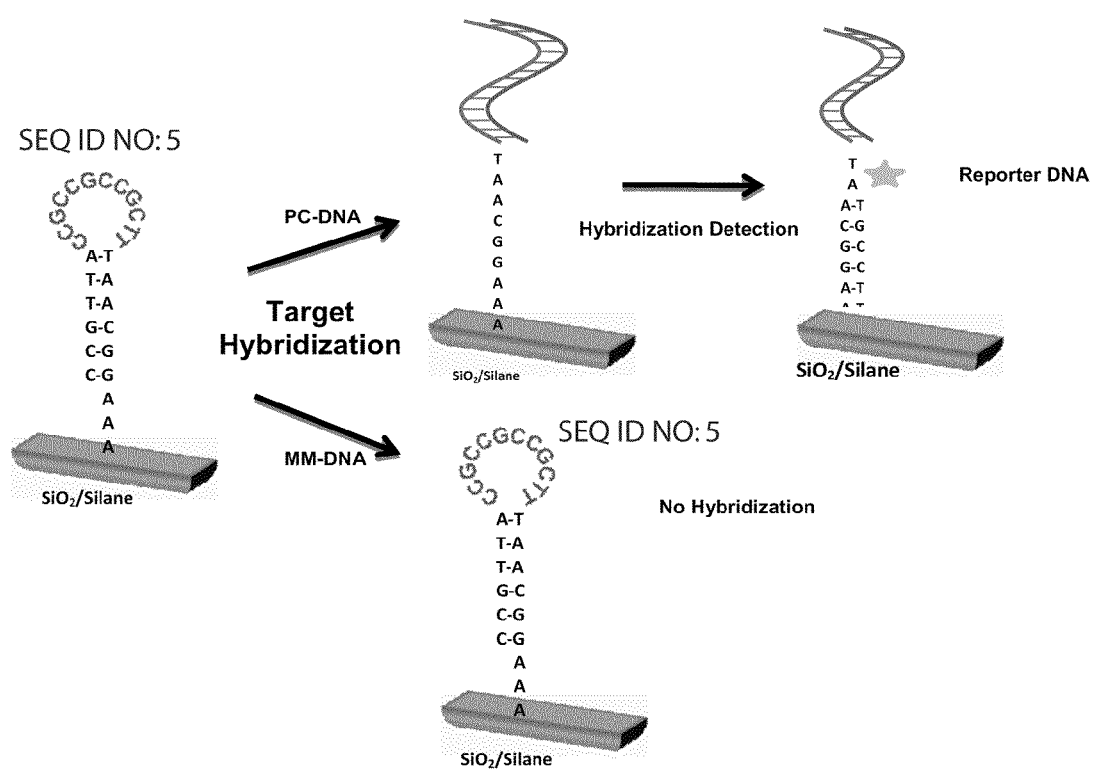

Chip 2: silane+hairpin loop probes+perfectly complementary target+gold nanoparticle reporter conjugate Chip 3: silane+hairpin loop probes+single base mismatched target+gold nanoparticle reporter conjugate Chip 4: silane+hairpin loop probes+gold nanoparticle reporter conjugate FIG. 10 shows the nucleic acid sequences for the perfectly complementary ("PC") target and single base mismatched ("MM") target along with the attached hairpin loop probe and the nanoparticle reporter conjugate ("HD-GNP") used in Example 1.

Figure 11:
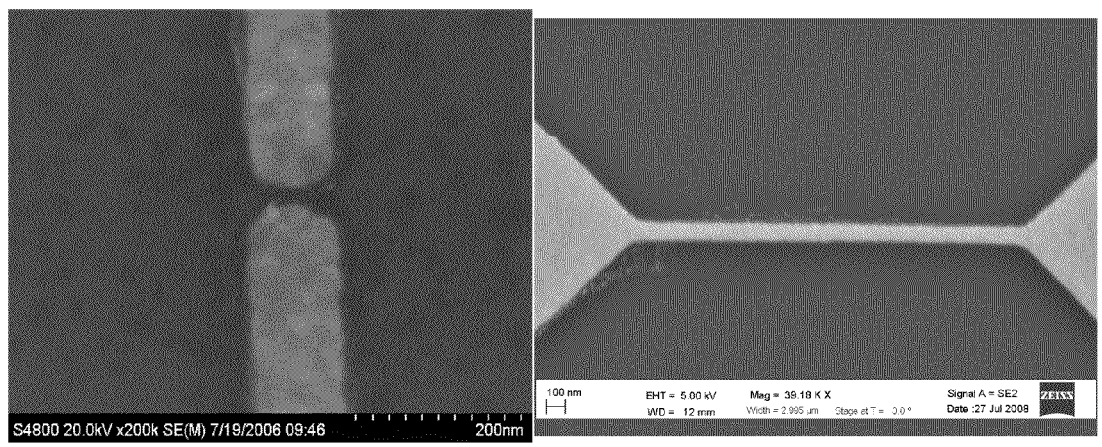

FIG. 11 shows the gold electrodes with a nanogap prior to attachment of the hairpin loop probes of one embodiment of the invention.

Figure 12:
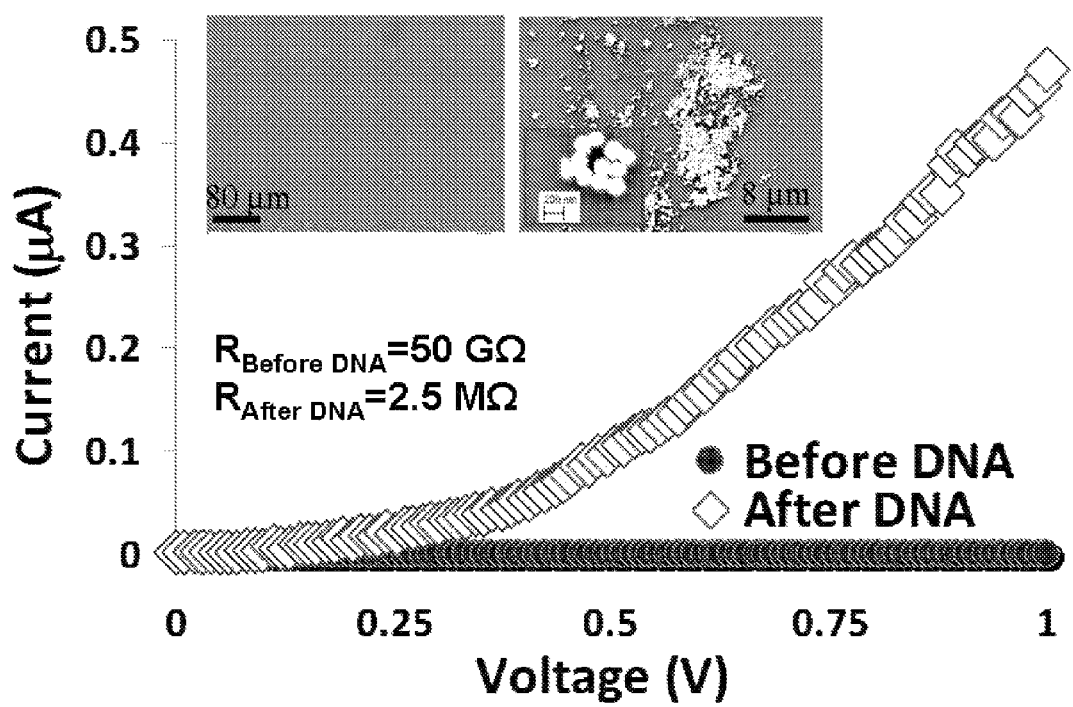

FIG. 12 is a plot showing a comparison of current-voltage (I-V) characteristics of the a nanogap before and after treating the hairpin loop probe with a perfectly complementary target and the nanoparticle reporter conjugates.

Figure 13A:
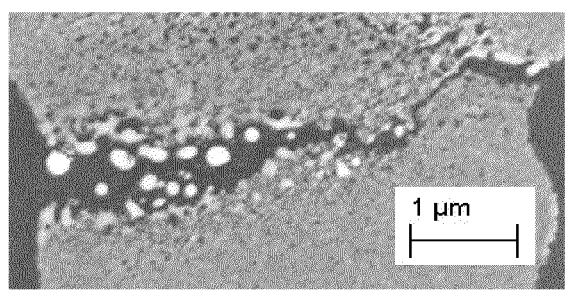
Figure 13B:
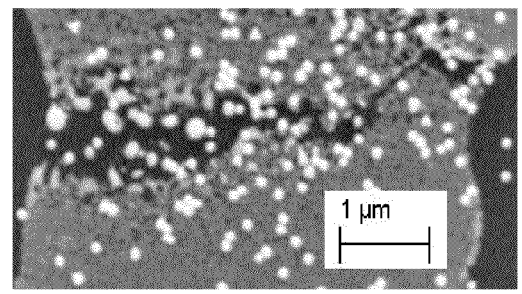

FIG. 13A is a scanning electron micrograph of the nanogap prior to hybridization between the oligonucleotide target and the perfectly complementary oligonucleotide hairpin loop probe. FIG. 13B is a scanning electron micrograph of the nanogap after hybridization between the oligonucleotide target and the perfectly complementary oligonucleotide hairpin loop probe.

Figure 14:
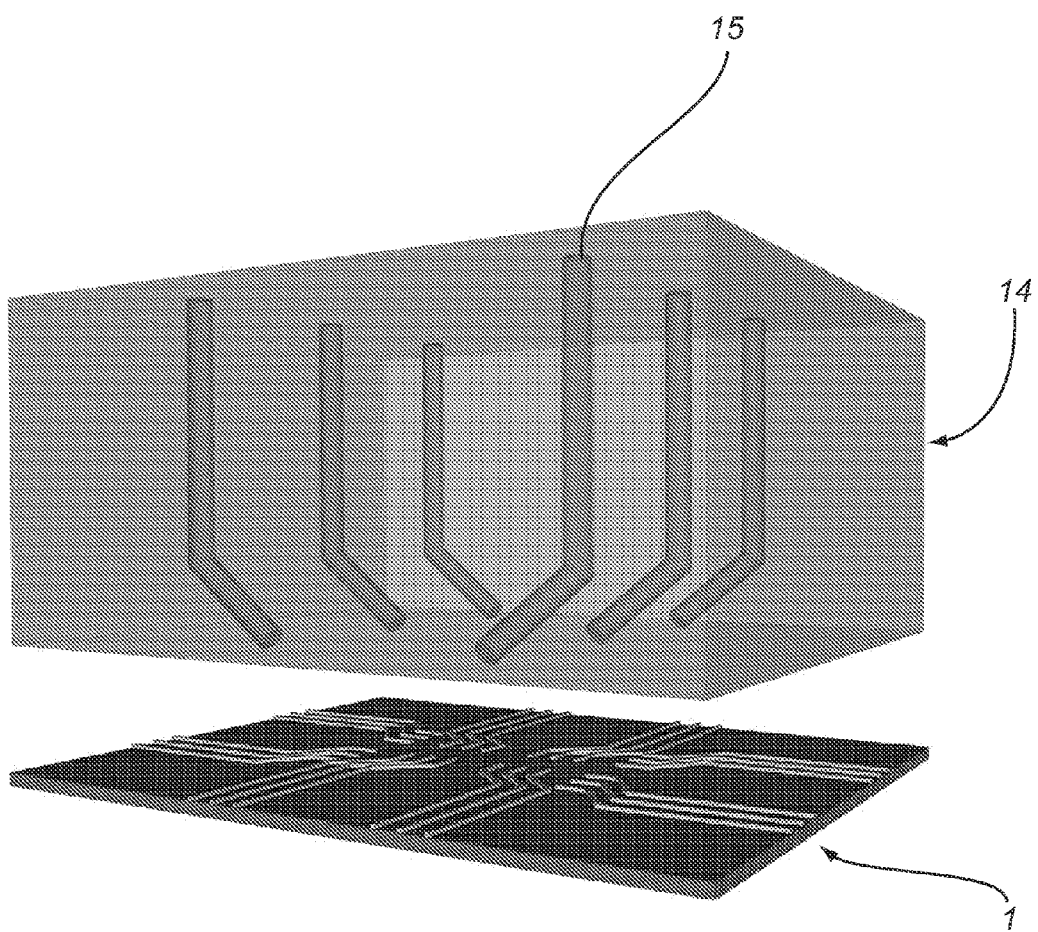

FIG. 14 is a schematic diagram showing one embodiment of the invention where a chip and a cover block with microchannels for fluid handling are shown.

Figure 15:
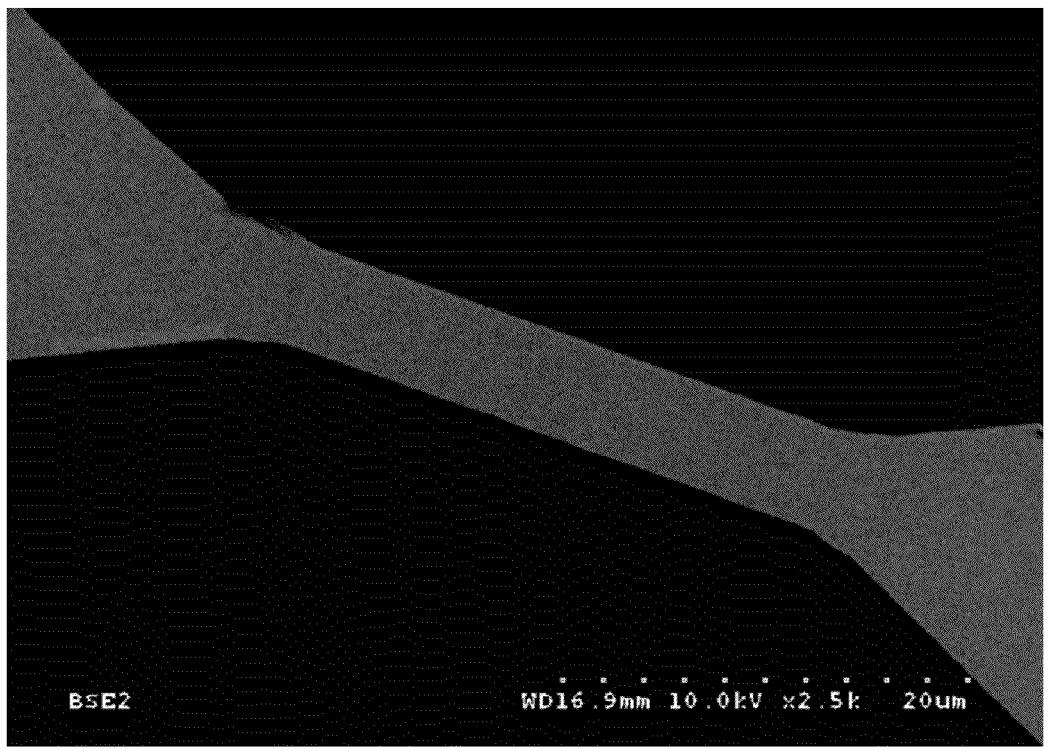

FIG. 15. SEM micrograph of metal line defined with optical lithography

Figure 16A:
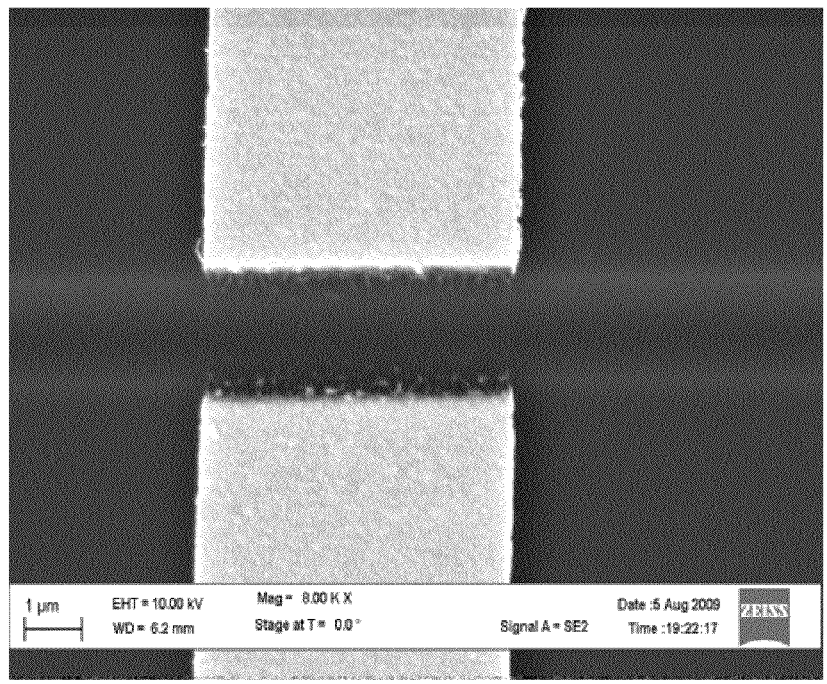
Figure 16B:
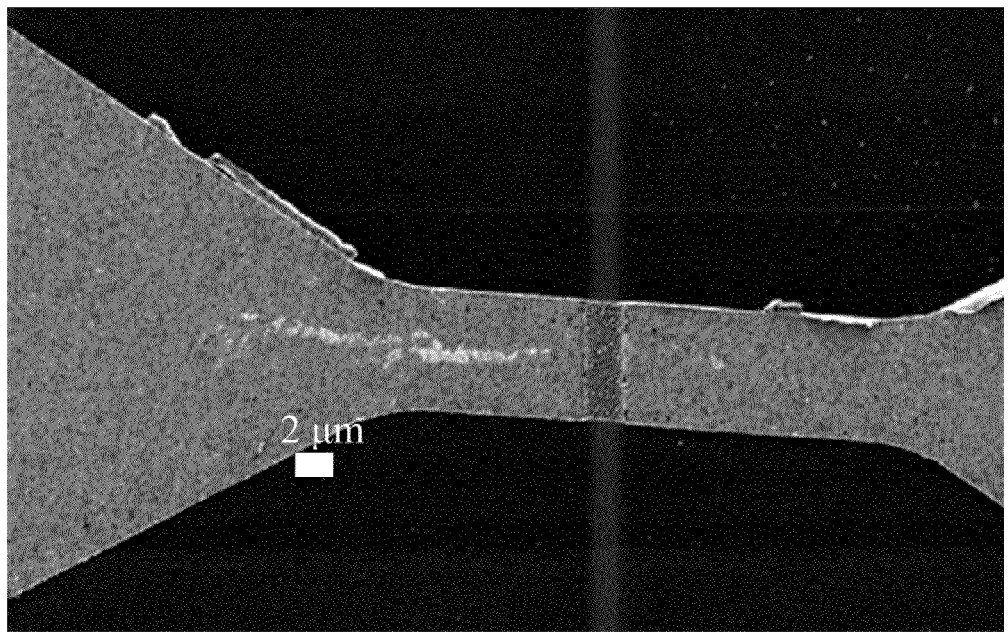
Figure 16C:
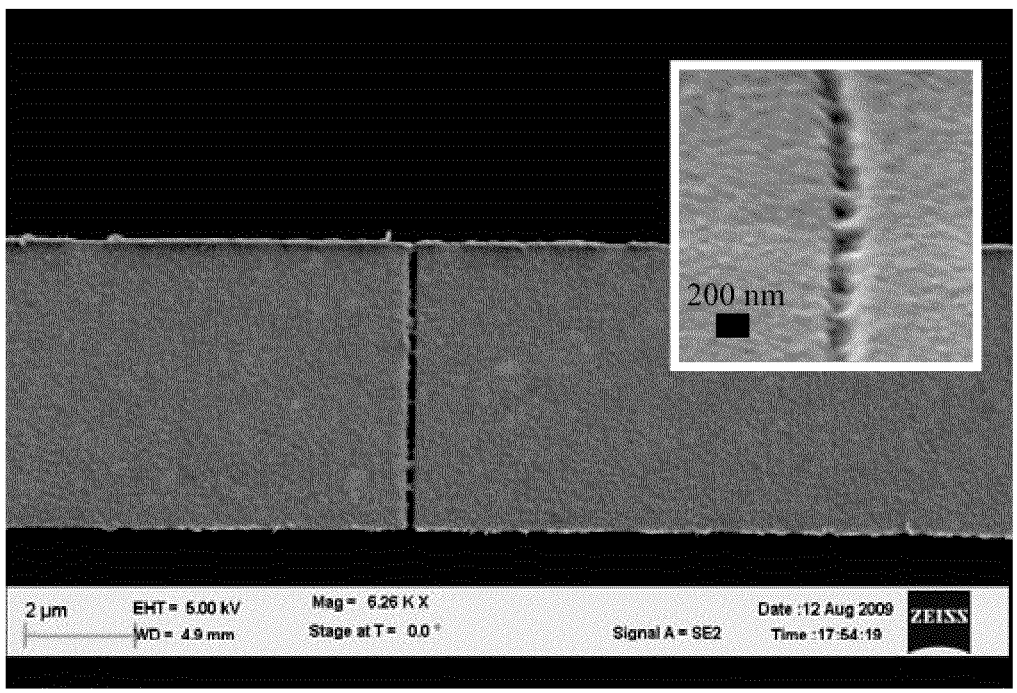

FIGS. 16A to 16C show scanning electron micrographs having FIB scratches at different accelerating voltages, milling currents and time of scratching exposure: (a) 30 KV, 100 pA, 120 seconds (b) 30 KV, 20 pA, 120 seconds, and (c) 30 KV, 1 pA, 60 seconds. Inset to FIG. 16C shows an angled magnified view of the FIB scratch.

Figure 17:
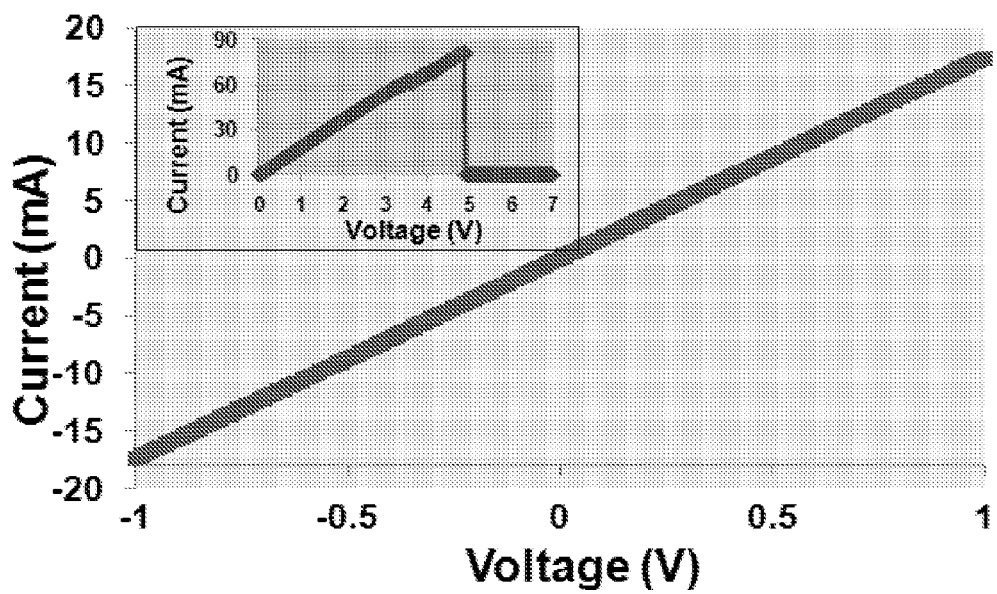

FIG. 17 shows representative I-V data of metal lines after the FIB scratch. The inset shows the drop in current through metal line as the electromigration resulted in complete break of the metal line resulting into nanoscale break junctions.

Figure 18:
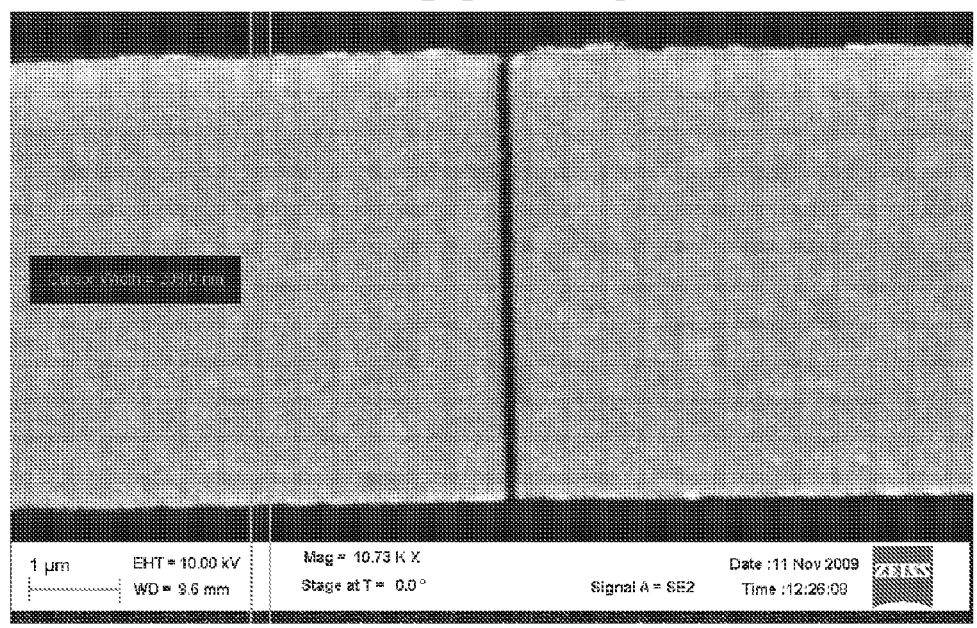

FIG. 18 is a scanning electron micrograph showing the nanogap between the gold electrodes.

Figure 19:
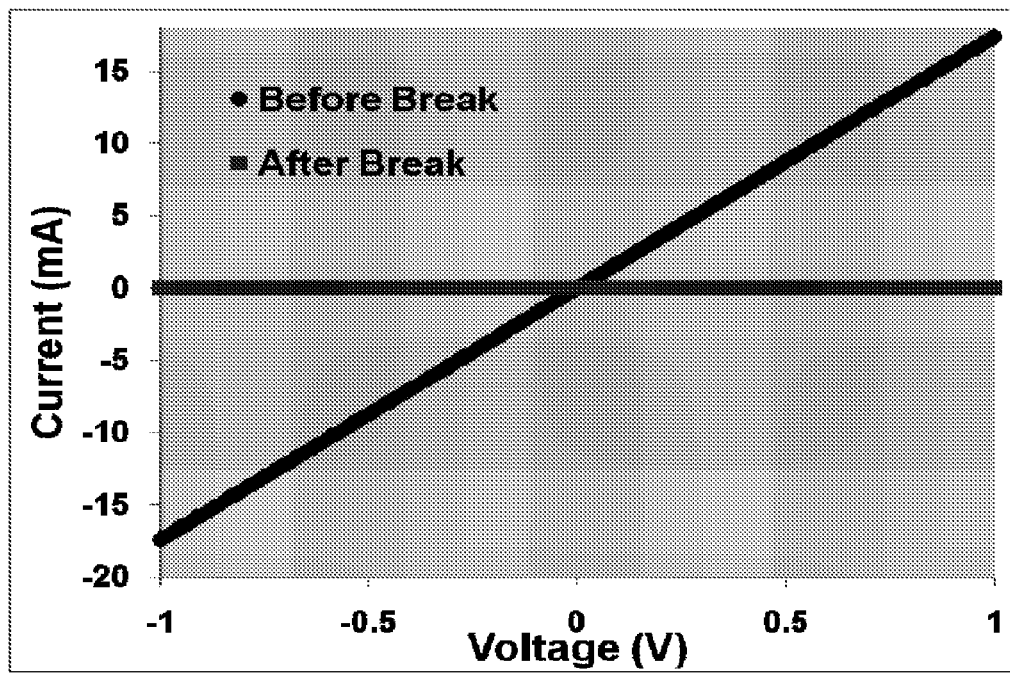

FIG. 19 shows the comparison I-V measurements before and after the break in the formation of the nanogap.

Figure 20:
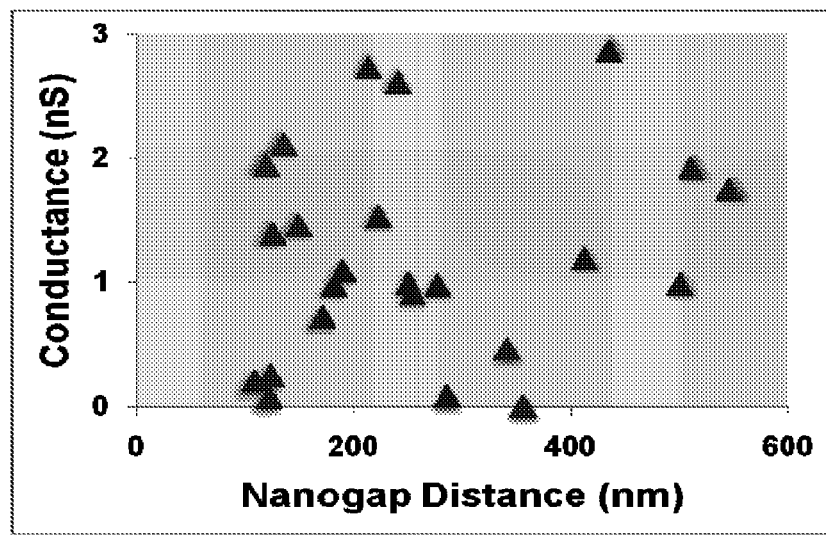

FIG. 20 shows the measured conductance (after break) plotted against the distance between two electrodes of break junctions.

DETAILED DESCRIPTION OF THE INVENTION

The invention provides devices, systems, and methods for detecting nucleic acid hybridization, including single nucleic base mutations, are disclosed, using surface-tethered hairpin loop oligonucleotide probes and metal-nanoparticles conjugated to a hybridization detection sequence that is capable of binding the stem of region of the opened hairpin loop oligonucleotide probe, without the use of labeling or target modification.

Reference will now be made in detail to the preferred embodiments of the invention, examples of which are illustrated in the drawings and the examples. This invention may, however, be embodied in many different forms and should not be construed as limited to the embodiments set forth herein. In addition and as will be appreciated by one of skill in the art, the invention may be embodied as a product, method, system or process.

Unless defined otherwise, all technical and scientific terms used herein have the same meaning as commonly understood to one of ordinary skill in the art to which this invention belongs. The following definitions are provided for the full understanding of terms used in this specification.

As used herein, the article "a," "an," and "the" means "at least one", unless the context in which the article is used clearly indicates otherwise.

As used herein, the term "nucleic acid" as used herein means a polymer composed of nucleotides, e.g. deoxyribonucleotides or ribonucleotides.

As used herein, the terms "ribonucleic acid" and "RNA" as used herein mean a polymer composed of ribonucleotides.

As used herein, the terms "deoxyribonucleic acid" and "DNA" as used herein mean a polymer composed of deoxyribonucleotides.

As used herein, the term "oligonucleotide" denotes single- or double-stranded nucleotide multimers of from about 2 to up to about 100 nucleotides in length. Suitable oligonucleotides may be prepared by the phosphoramidite method described by Beaucage and Carruthers, *Tetrahedron Lett.*, 22:1859-1862 (1981), or by the triester method according to Matteucci, et al., *J. Am. Chem. Soc.*, 103:3185 (1981), both incorporated herein by reference, or by other chemical methods using either a commercial automated oligonucleotide synthesizer or VLSIPS™ technology. When oligonucleotides are referred to as "double-stranded," it is understood by those of skill in the art that a pair of oligonucleotides exist in a hydrogen-bonded, helical array typically associated with, for example, DNA. In addition to the 100% complementary form of double-stranded oligonucleotides, the term "double-stranded," as used herein is also meant to refer to those forms which include such structural features as bulges and loops, described more fully in such biochemistry texts as Stryer, Biochemistry, Third Ed., (1988), incorporated herein by reference for all purposes.

As used herein, the term "polynucleotide" refers to a single or double stranded polymer composed of nucleotide monomers of generally greater than 100 nucleotides in length and up to about 8,000 or more nucleotides in length.

As used herein, the term "cDNA" means a complementary DNA molecule made as a copy of mRNA amplified using PCR for deposition on arrays. cDNAs can range from about 100 bp to about 8,000 bp, where average cDNAs are typically 1 to 2 kb in length.

As used herein, "polypeptide" refers to a compound made up of a single chain of D- or L-amino acids or a mixture of D- and L-amino acids joined by peptide bonds. Generally, peptides are about 2 to about 50 amino acids in length.

As used herein, the term "array" means an substrate having a plurality of binding agents (probes) stably attached to its surface, where the binding agents (probes) are arranged in a spatially defined and physically addressable manner across the surface of the substrate in any of a number of different patterns. Generally, at least two of the plurality of binding agents (probes) are different.

As used herein, the term "complementary" refers to the topological compatibility or matching together of interacting surfaces of a probe molecule and its target. Thus, the target and its probe can be described as complementary, and furthermore, the contact surface characteristics are complementary to each other.

As used herein, the term "hybridization" refers to a process of establishing a non-covalent, sequence-specific interaction between two or more complementary strands of nucleic acids into a single hybrid, which in the case of two strands is referred to as a duplex.

As used herein, the term "anneal" refers to the process by which a single-stranded nucleic acid sequence pairs by hydrogen bonds to a complementary sequence, forming a double-stranded nucleic acid sequence, including the reformation (renaturation) of complementary strands that were separated by heat (thermally denatured).

As used herein, the term "melting" refers to the denaturation of a double-stranded nucleic acid sequence due to high temperatures, resulting in the separation of the double strand into two single strands by breaking the hydrogen bonds between the strands.

As used herein, the term "probe" refers to a surface-immobilized molecule that can be recognized by a particular target.

As used herein, the term "target" refers to a molecule that has an affinity for a given probe. Targets may be naturally-occurring or man-made molecules. Also, they can be employed in their unaltered state or as aggregates with other species.

As used herein, the term "biological chip," "chip", or "biosensor" refers to a substrate having a surface to which one or more arrays of probes is attached.

As used herein, the term "wafer" refers to a substrate having a surface to which a plurality of probe arrays are attached. On a wafer, the arrays are physically separated by a distance of at least about a millimeter, so that individual chips can be made by dicing a wafer or otherwise physically separating the array into units having a probe array.

As used herein, the term "hairpin structure" refers to an oligonucleotide that contains a double-stranded stem segment and a single-stranded loop segment wherein the two polynucleotide or nucleic acid strands that form the double-stranded stem segment is linked and separated by the single polynucleotide or nucleic acid strand that forms the loop segment. The "hairpin structure" can also further comprise 3' and/or 5' single-stranded region(s) extending from the double-stranded stem segment.

As used herein, the phrase "two perfectly complementary nucleotide sequences" refers to a nucleic acid duplex wherein the two nucleotide strands match according to the Watson-Crick base pair principle, i.e., A-T and C-G pairs in DNA:DNA duplex and A-U and C-G pairs in DNA:RNA or RNA:RNA duplex, and there is no deletion or addition in each of the two strands.

To more fully understand the invention, the various embodiments will be described with respect to the figures.

Figure 6:
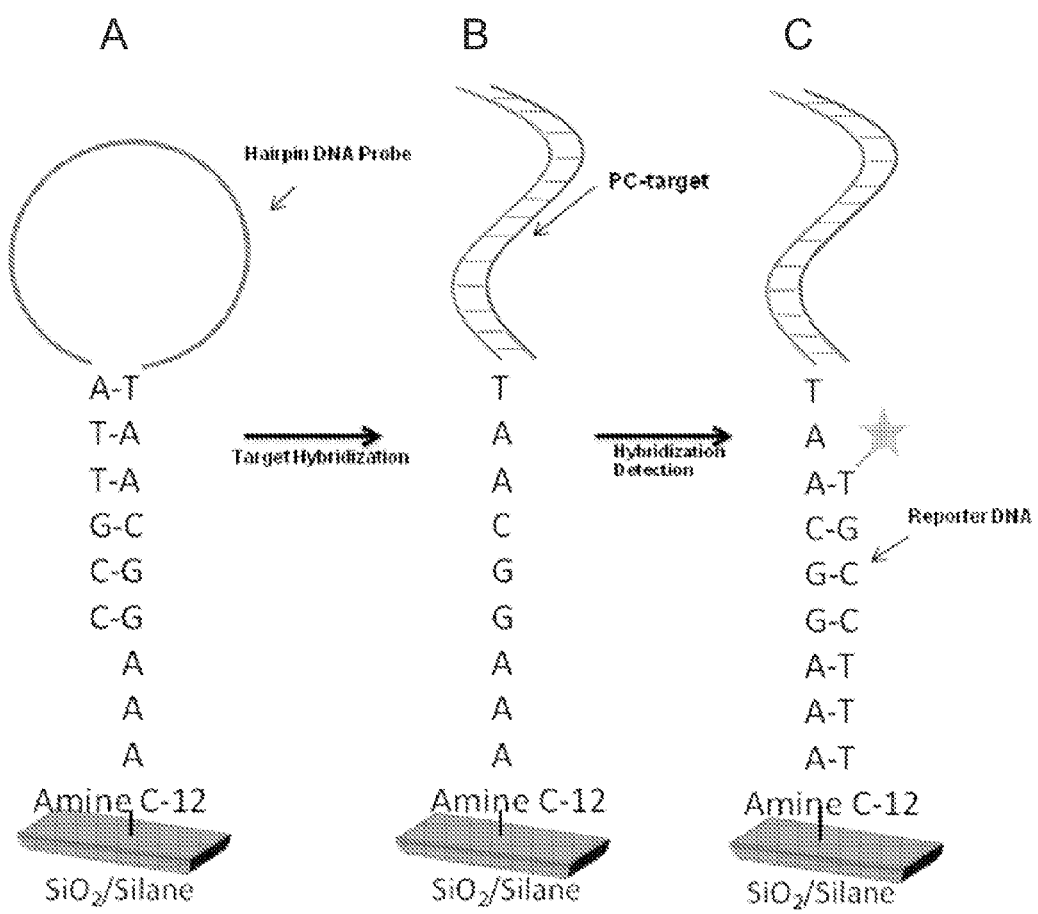
FIG. 6A is a schematic view of a hairpin loop oligonucleotide probe covalently attached via an amine-C12 on the silicon dioxide/silane surface.
FIG. 6B is a schematic of a hairpin loop oligonucleotide probe covalently attached via an amine-C12 on the silicon dioxide/silane surface after a target molecule hybridizes with the loop portion of the probe. This hybridization exposes the stem portion of the probe permitting the hybridization of a subsequently added nanoparticle reporter conjugate, which changes the electrical current across the electrodes where the probes are attached, as shown in FIG. 6C. In this embodiment, the k-ras probe starts with CCGTT and covers the whole loop.
Figure 7A:
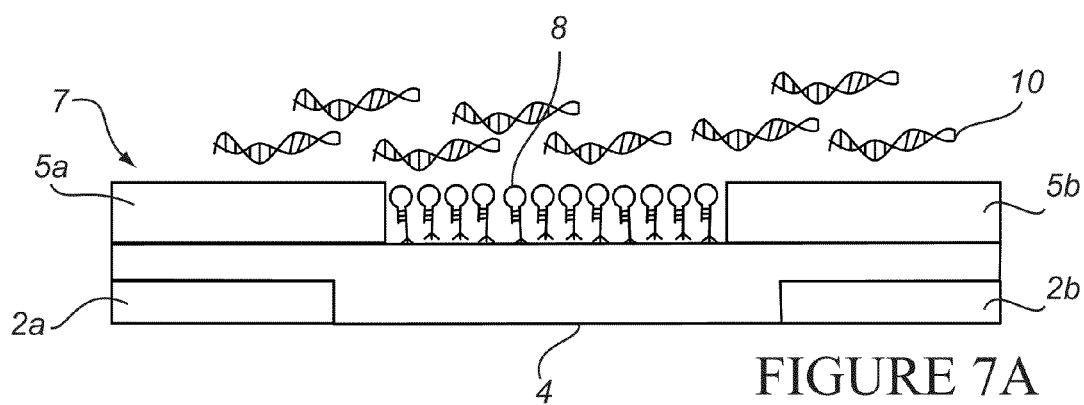
FIGS. 7A to 7C depict different stages of the hybridization process.
Figure 7B:
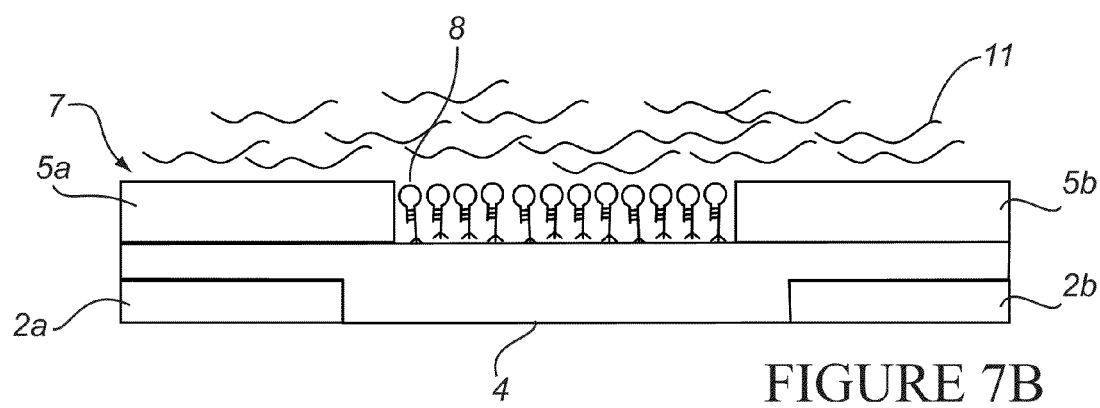
Figure 7C:
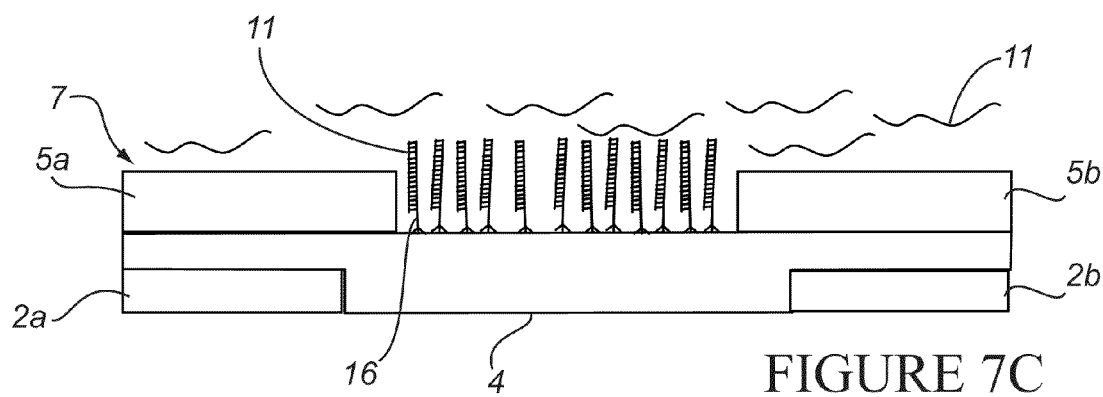

FIGS. 7A to 7C show the different stages of the target hybridization process, while FIGS. 6A to 6C show the details at an individual probe of one exemplary embodiment, where a hairpin loop oligonucleotide probe of a particular sequence is covalently attached via an amine-C12 on the silicon dioxide/silane surface. FIG. 6B is a schematic of a hairpin loop oligonucleotide probe covalently attached via an amine-C12 on the silicon dioxide/silane surface after a target molecule hybridizes with the loop portion of the probe. This hybridization exposes the stem portion of the probe permitting the hybridization of a subsequently added nanoparticle reporter conjugate, which changes the electrical current across the electrodes where the probes are attached, as shown in FIG. 6C. In this embodiment, the k-ras probe starts with CCGTT and covers the whole loop.

FIGS. 7A to 7C depict different stages of the hybridization process. FIG. 7A shows double-stranded oligonucleotide target molecules 10 present at the nanogap 6 of the electrodes 5a, 5b (heating elements 2a, 2b and hairpin loop oligonucleotide probes 8 also shown). FIG. 7B shows melting of the double-stranded oligonucleotide target molecules 10 to single-stranded oligonucleotide target molecules 11 present at the nanogap of the electrodes nanogap 6 of the electrodes 5a, 5b. FIG. 7C shows hybridization of the single-stranded oligonucleotide target molecules 10 present at the nanogap 6 of the electrodes nanogap 6 of the electrodes 5a, 5b to the oligonucleotide probes, causing the hairpin loop formation to open 13 and also exposing unhybridized nucleotide bases in the stem region of the oligonucleotide probes.

Devices

In one embodiment, the invention is directed to devices, comprising:
a thermally responsive, electrically insulating substrate;
at least one heating element; and
a first detecting unit, comprising:
a first electrode and a second electrode separated by a nanogap; and
a plurality of first oligonucleotide probes attached to said substrate in said nanogap;
wherein said first oligonucleotide probes are in a hairpin loop formation and have the same nucleic acid sequence; and
wherein said first oligonucleotide probes comprise an optional spacer, a loop, and a stem region, said stem region being double-stranded.

In certain embodiments, the device further comprises:
a plurality of additional heating elements capable of forming a temperature gradient.

In certain embodiments, including those involving arrays, the device further comprises:
a plurality of second detecting units, comprising:
a first electrode and a second electrode separated by a nanogap; and
a plurality of second oligonucleotide probes attached to said substrate in said nanogap;
wherein said second oligonucleotide probes are in a hairpin loop formation and have the same nucleic acid sequence; and
wherein said second oligonucleotide probes comprise an optional spacer, a loop, and a stem region, said stem region being double-stranded;
wherein said second oligonucleotide probes are the same or different from said first oligonucleotide probes in said first detecting unit; and
wherein said second oligonucleotide probes are the same or different from other second oligonucleotide probes in said plurality of second detecting units.

In certain embodiments, the device further comprises:
a plurality of microfluidic channels; and
an optional cover.

In certain embodiments of the device, the first detecting unit is located on the surface of said substrate.

In certain embodiments of the device, said at least one heating element is located in a first layer; and said first electrode and said second electrodes are located in a second layer.

The device may be fabricated as a single layer or, preferably, as multiple layer, using standard and advanced silicon fabrication techniques. In preferred embodiments, there are two functional layers. The first layer has heating elements, preferably embedded heating nano-plates. The second layer has electrical nano-electrodes.

Standard complementary metal-oxide-semiconductor (CMOS) processes may be used to create an array of detecting units on a single wafer for multiple nucleic acid detection with printed circuit board (PCB) data acquisition and analysis capability.

The design of the chip gives an array of detecting units in which hundreds (n2) of interaction sites may be addressed using a few (2n) probing pads. The probing pads in turn are addressed and controlled using sensitive electronics and software in the manner that pixels in a thin film transistor (TFT) television. This provides an integrated system with on-chip circuitry for data gathering, storage, and analysis. Suitable techniques for addressing the interaction sites at the electrodes in the array are described in the following references, which are incorporated herein by reference in their entirety:

A. Hassibi and T. H. Lee, *IEEE Sensors Journal*, 6(6), 1380-1388, (2006);

W. F. Aerts, S. Verlaak, and P. Heremans, IEEE Transactions on Electron Devices, 49(12), 2124-2130, (2002); and A. Hassibi, "Integrated Microarrays" Section in *Electrical Engineering*. 2005, Stanford University Palo Alto, Calif. p. 141.

Substrate

The devices of the invention include a thermally responsive, electrically insulating substrate. The substrate is preferably flat but may take on a variety of alternative surface configurations. For example, the substrate may contain raised or depressed regions on which the probes are located. The substrate and its surface preferably form a rigid support on which the probes can be attached. For instance, the substrate may be any thermally responsive, electrically insulating materials. Suitable substrates include, but are not limited to, functionalized glass, Si, Ge, GaAs, GaP, $SiO_2$, $SiN_4$, modified silicon, or any one of a wide variety of gels or polymers such as (poly)tetrafluoroethylene, (poly)vinylidenedifluoride, polystyrene, polycarbonate, polypropylene, or combinations thereof. The substrate may be deposited by chemical vapor deposition. Other substrate materials and deposition methods will be readily apparent to those of skill in the art upon review of this disclosure. In a preferred embodiment, the substrate is flat glass or silica with a silicon dioxide layer grown on the surface to provide electrical insulation.

The hairpin loop oligonucleotide probes useful in the devices, systems, and methods of the invention are attached to the surface of the chip. In one embodiment, the chip is first cleaned, for example, using oxygen plasma at 200 W in Ar+$O_2$. This treatment also makes the surface hydrophilic. Surface functionalization of the chips may be done in a nitrogen glove box with controlled temperature, as described in S. M. Iqbal, D. Akin, and R. Bashir, *Nature Nanotechnology*, 2(4), 243-248 (2007), incorporated herein by reference. For example, on a clean chip, a self-assembled monolayer (SAM) of 3-aminopropyltrimethoxysilane (APTMS) (5% solution in 95% ethanol) is reacted with the hydroxyls on the surface to provide silane functionality to the surface of the chip. Next, the silane-functionalized surface is reacted with p-phenylene diisothiocyanate (PDITC) (dissolved in dimethylformamide containing 10% pyridine) as a bifunctional linker. Finally, the chip is immersed in a solution containing the hairpin loop oligonucleotide probes. Once attached, the probe molecule may be heat-cycled in buffer, such as TrisEDTA (TE) buffer, multiple times to ensure that all molecules form the requisite hairpin loop structures. To deactivate the unreacted surface-bound isothiocyanate groups, the chips may be immersed in a blocking solution, such as 50 mM 6-amino-1-hexanol and 150 nM DPEA in dimethylformamide (DMF) for 2 hours after which the substrate is sequentially washed with, for example, DMF, acetone, deionized water, and dried in a stream of nitrogen.

Heating Elements

In certain embodiments, the heating element is embedded in said substrate. FIGS. 4A and 4B show one embodiment where the heating elements are embedded in the substrate.

The heating elements useful in the devices, systems, and methods of the invention may comprise any material suitable for preparing electrodes, including but not limited to, gold, silver, titanium, copper, and combinations thereof.

Figure 1A:
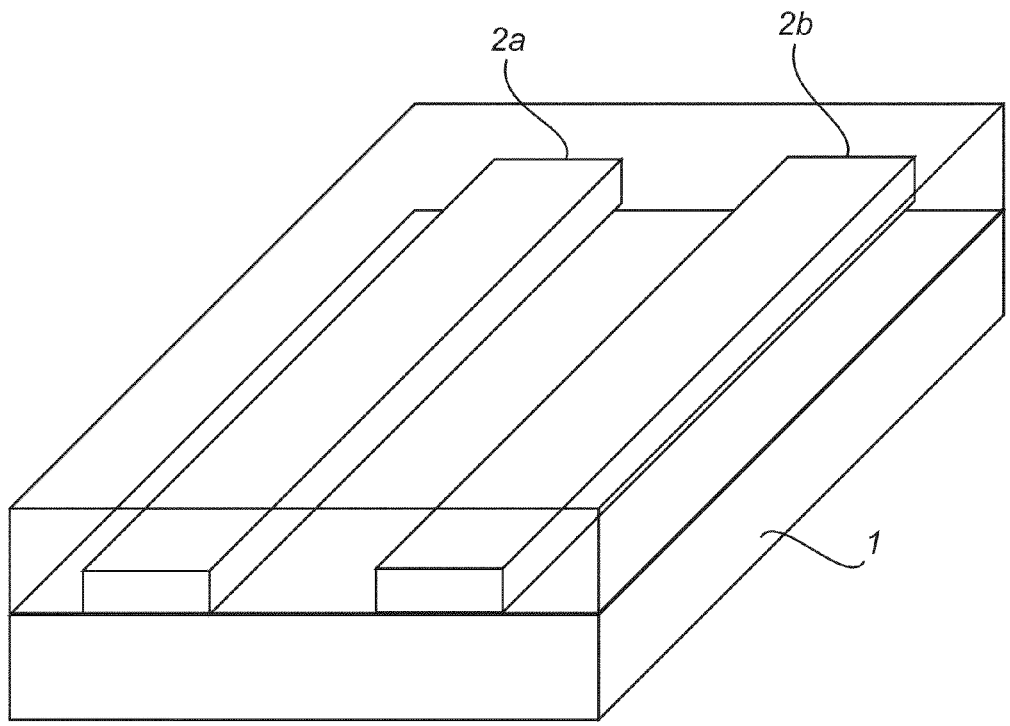
FIG. 1A is a three-dimensional view of metal nanoplates as heating elements 2a, 2b embedded on a silicon dioxide chip 1.
Figure 1B:
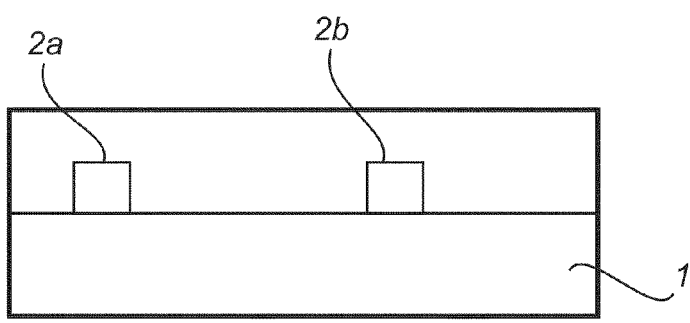
FIG. 1B is a side view of the metal nanoplates as heating elements 2a, 2b embedded on the silicon dioxide chip 1, shown in FIG. 1A.
Figure 2:
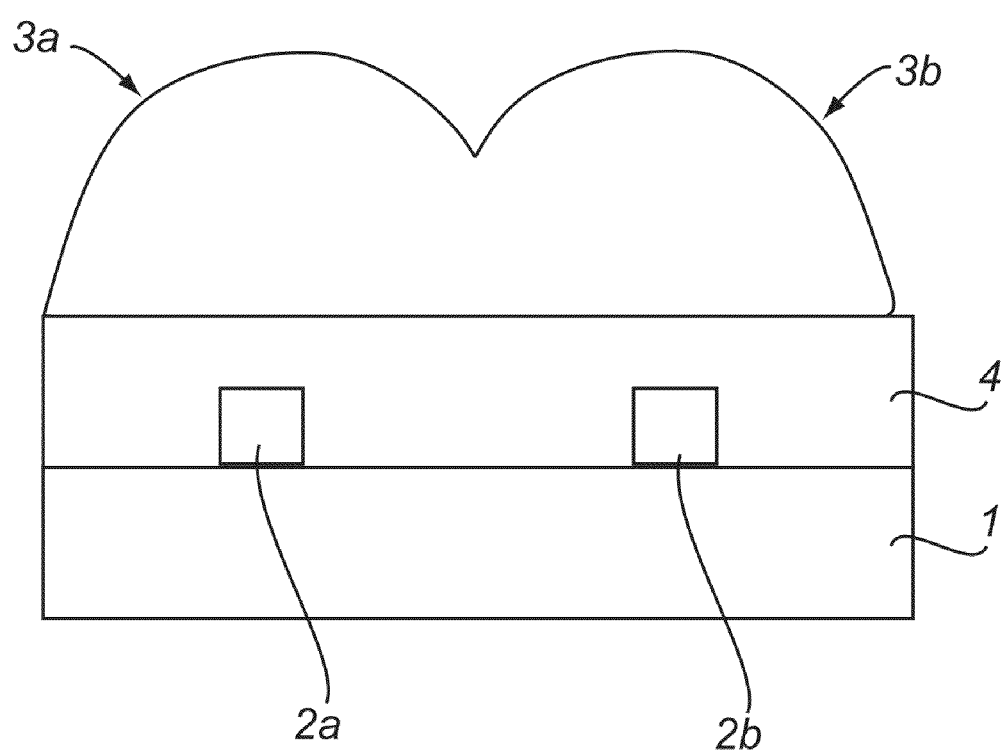
FIG. 2 is a side view of metal nanoplates as heating elements 2a, 2b embedded on silicon dioxide chip 1 showing typical temperature gradients 3a, 3b for each heating element 2a, 2b.

In certain embodiments, the devices of the invention have an array of heating elements. The heating elements are metal nanoplate heater elements 2a, 2b embedded on silicon dioxide chip 1, as shown in FIG. 1A and FIG. 1B. The heating elements may be fabricated using standard lithography and can provide precise control of temperature fields, as described in A. Jain, K. D. Ness, H. A. Fishman, and K. E. Goodson, *Microtechnology in Medicine and Biology*, 2005, 3$^{rd}$ IEEE/EMBS Special Topic Conference on 2005: 398-399, incorporated herein by reference. FIG. 2 shows typical temperature gradients from individual nanoplates 2a, 2b. The individual heating elements may be addressed in groups to enable temperature cycling for various operations of the device, including, but not limited to, focusing of oligonucleotide targets toward the nanogap between the sets of electrodes 5a, 5b, melting of double stranded oligonucleotide targets (without melting and denaturing the hairpin loop oligonucleotide probes causing loss of sensitivity against mismatches), and recycling of the oligonucleotide probes.

Figure 3A:
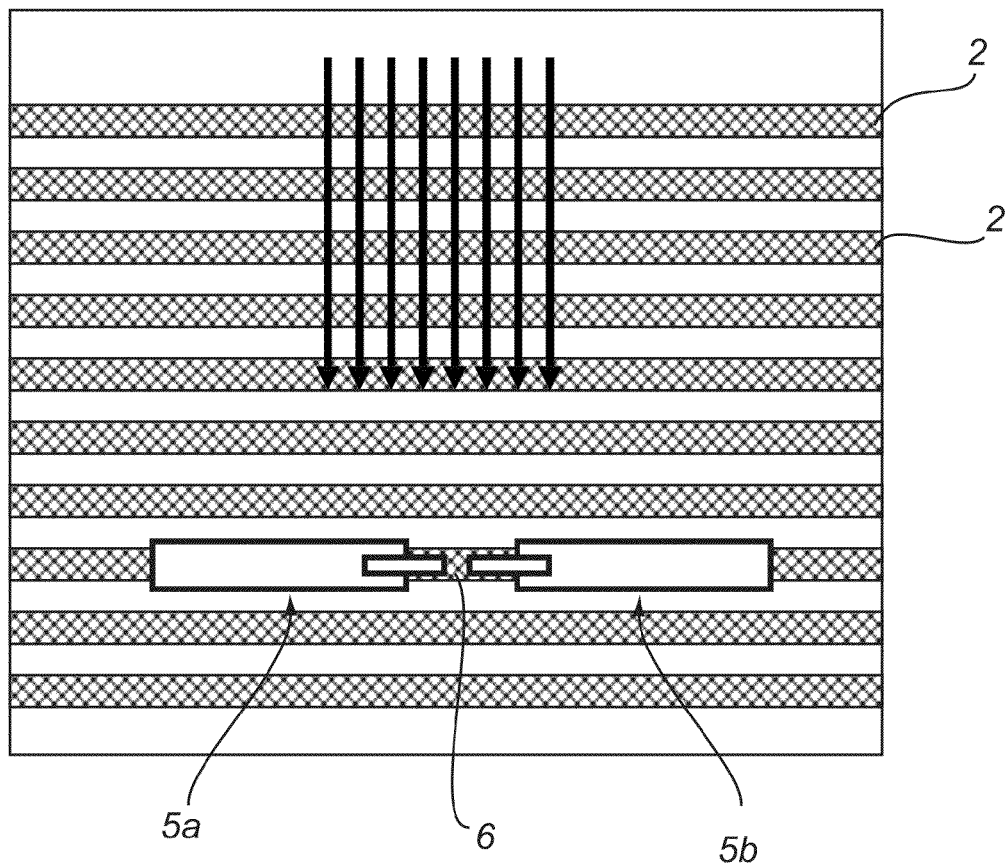
FIG. 3A is a top view of metal nanoplates as heating elements 2a, 2b embedded on a silicon dioxide chip 1 with nanogap electrodes 5a, 5b using a temperature gradient to focus or move oligonucleotide target molecules 10 toward the nanogap electrodes 5a, 5b.
Figure 3B:
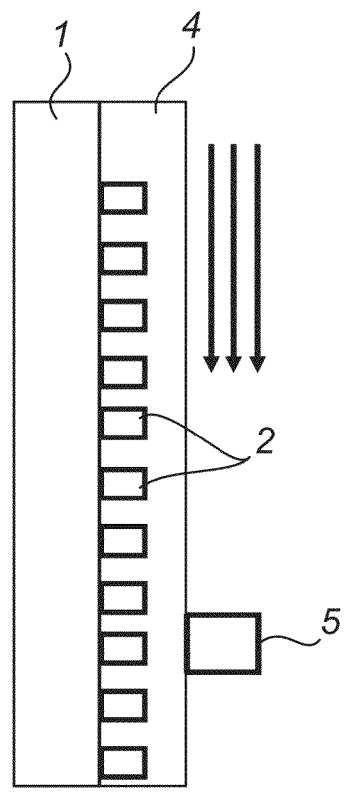
FIG. 3B is a side view of metal nanoplates as heating elements 2a, 2b embedded on a silicon dioxide chip 1 with nanogap electrodes 5a, 5b showing the movement of the buffer solution containing the oligonucleotide target molecules 10 toward the nanogap electrodes 5a, 5b.

In operation as shown in FIGS. 3A and 3B, a solution containing at least one buffer and the double-stranded oligonucleotide (DNA, cDNA, or RNA fragment) is flowed into the denaturation chambers (not shown) from the microfluidic channel (not shown) at a temperature gradient at least as high as the melting temperature ($T_m$) of the double-stranded oligonucleotide target before being carried over the nanogap of the electrodes. The black arrows indicate the flow of the solution.

The embedded heating elements serve multiple purposes, including:
- on-chip/device denaturing of the double-stranded oligonucleotide target molecules, removal of secondary structures of cDNA, competitive capture with the surface-bound oligonucleotide probe;
- recycling capability of the device for the next batch of target solution by denaturing the probe-target duplex; and
- temperature gradient focusing to concentrate the solution containing the oligonucleotide target at the nanogap of the electrodes.

The heating elements may be covered in a thermally-responsive but electrically-insulating material layer, such as silicon dioxide, deposited, for example, by chemical vapor deposition (CVD).

Electrodes and Nanogap

In certain embodiments, the first and second electrodes comprise a metal selected from the group consisting of gold, silver, titanium, copper, or a combination thereof.

Figure 5A:
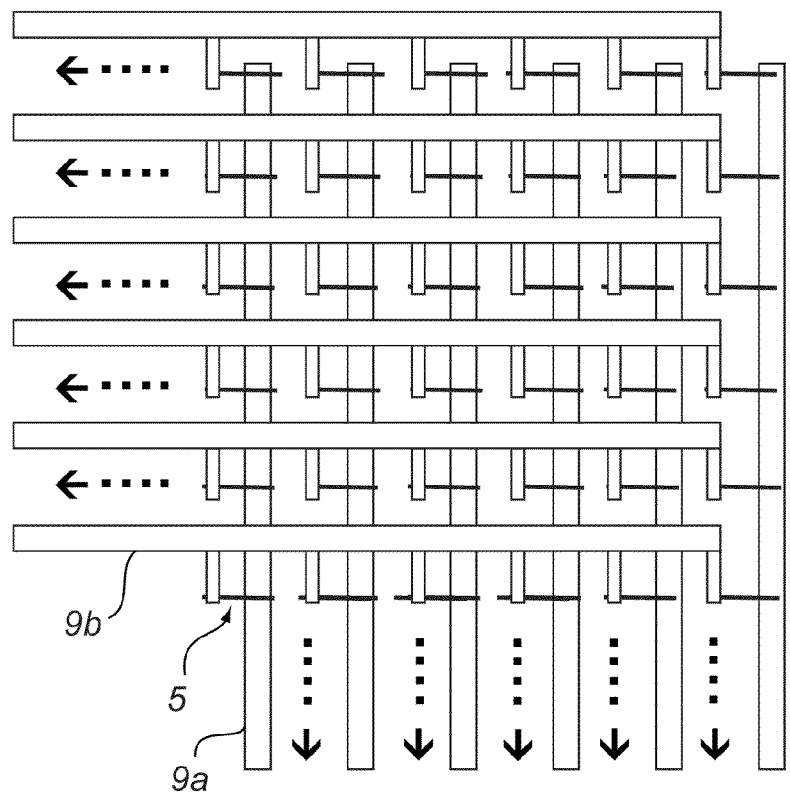
FIG. 5A is a top view of one embodiment showing two bus lines 9a, 9b used to address the individual set of electrodes 5a, 5b with a nanogap 6 fabricated with nanoimprint lithography. Arrows indicate the extension of similar structures to cover the whole chip area.

Nanoimprint lithography may be used to fabricate the electrodes with the nanogaps. The electrodes may formed into an array where each nanogap is individually addressed with metal lines (bus-bars), preferably running at right angles. Each mutually-insulated intersection of the addressing lines contacts one nanogap electrode pair that serves as the binding and sensing site of the probe-target hybridization. The bus lines may be fabricated in two layers with electrical isolation between the two layers achieved by chemical vapor deposition (CVD) of silicon nitride. FIG. 5A is a top view of one embodiment showing two bus lines 9a, 9b used to address the individual set of electrodes 5a, 5b with a nanogap 6 fabricated with nanoimprint lithography. Arrows indicate the extension of similar structures to cover the whole chip area. In certain embodiments, microfluidic channels run exactly on top of the nanogap electrodes, thus reducing any cross-talk between probe and target molecules of successive rows.

Figure 5B:
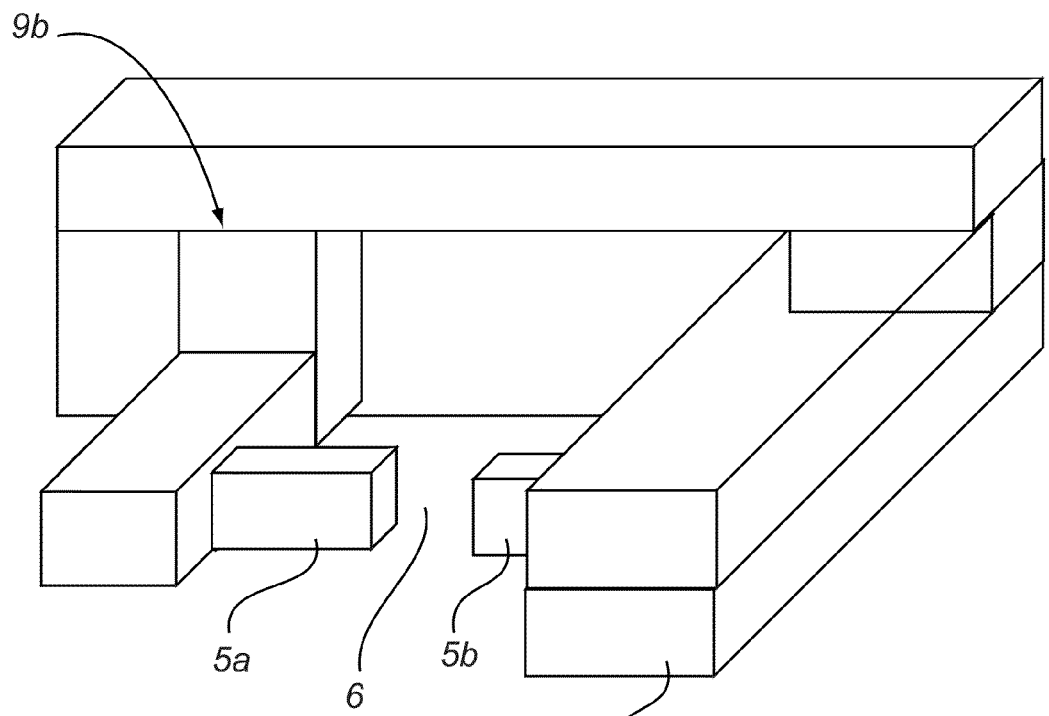
FIG. 5B is a blown up schematic (not to scale) of FIG. 5A showing the individual set of electrodes 5a, 5b with a nanogap 6, one electrode addressing/measuring bus 9a covered with silicon nitride and the other electrode addressing/measuring bus 9b. Oligonucleotide probe molecules (not shown) are attached to the chip in the nanogap 6 between the electrodes 5a, 5b.

FIG. 5B is a blown up schematic (not to scale) of FIG. 5A showing the individual set of electrodes 5a, 5b with a nanogap 6, one electrode addressing/measuring bus 9a covered with silicon nitride and the other electrode addressing/measuring bus 9b. Oligonucleotide probe molecules (not shown) are attached to the chip in the nanogap 6 between the electrodes 5a, 5b. This three-dimensional structure is adjacent to and aligned with embedded nanoplate heating elements discussed previously. The structure is covered with microfluidic channels. The electrical isolation may be achieved by sequential and automated measurement of each pair of electrodes. In preferred embodiments, the use of chemical vapor deposition (CVD) silicon dioxide results in a rough surface which facilitates the covalent attachment of the oligonucleotide probes to the surface of the substrate, thereby permitting an increased density of probes in the nanogap.

In certain embodiments, nanopatterns may be made on an oxidized silicon wafer using e-beam lithography (EBL). The EBL patterns may be used to fabricate the stamp for the nanoelectrode fabrication. The EBL patterns may be used to remove silicon dioxide and then silicon from the non-patterned areas using deep reactive ion etching (DRIE). Silicon dioxide acts as a hard mask during the process, resulting is a high aspect ratio nano-scale linear island features in silicon having the same dimensions as required the nanogap electrodes. The wafer may act as a stamping mask for NIL. In NIL, a polymer layer is spun on the wafer and a stamping wafer is compressed on the polymer to transfer the pattern. One stamp can be used multiple times and one stamping takes a few minutes to transfer the nano-scale patterns in the polymer. Standard lift-off process may be carried out to create the metal lines at the nanoscale from these stamp-defined patterns. In certain embodiments of the lift-off process, metal stays only in the NIL transferred nanoelectrode structure and the remainder of the metal lifts off in an ultra-sonicator assisted solvent soak. The first layer of addressing electrodes/bus may then be using standard optical lithography aligned to the nano-scale metal lines. The second layer of metal lines/bus may be deposited after CVD deposition of silicon nitride and reactive ion etch opening of small micron sized windows in the silicon nitride above the nanogap electrodes.

The use of three-dimensional interaction volume and interfacing space addresses the challenges of selectivity, high-yield fabrication, and sensitivity. Such three-dimensionality provides a means of not only improving selectivity by filtering unwanted species, but also allows reduced signal-to-noise ratios relative to what is attainable on planar substrates. The nanoelectrodes employed in the devices of the invention enable the majority of the electric field to interact with the biomolecules, resulting in highly sensitive detection.

Different methods may be used to fabricate the nanogap between a set of electrodes. A break junction may be prepared from an already fabricated electrode by, for example, a mechanically controlled break junction process or an electromigration break junction process. In certain preferred embodiments, the nanogap is formed by electromigration. FIG. 11 shows an scanning electron micrograph of a set of electrodes of gold with a nanogap.

In certain embodiments, the nanogap is about 10 nm to about 500 nm.

A break junction is the discontinuity or a nanoscale gap in a seemingly continuous structure. The most common visualization of a break junction is a gap formed in a thin metal strip by various methods. The nanoscale gap in the metal strip is the area of interest where the molecule is placed to make electrical contacts.

A mechanically-controlled break junction process is a process where a narrow bridge of metal is suspended above a flexible substrate. By bending the substrate, the metal bridge can be broken, and the distance between the ends can be controllably adjusted, with increments of much less than a pico meter.

To create a break junction using electromigration, an external electric field applied to a circuit causes large current density in the wires that connect the components. The electrons in a metal move under the influence of the large current density and if there is a charged defect in the metal, the momentum transfers from the conduction electrons to such a defect. As the momentum exchange becomes larger, a force is built up causing the mass movement of the atoms away from the defect causing breakdown of the metal at that point. In break junction, the break usually occurs in the constricted part of the metal in a controllable and self-limiting fashion. Normally, the breaking process consistently produces two metallic electrodes at typical separations.

There are several techniques to fabricate break junctions, well known in the art. Almost all of them follow the conventional process of thin film deposition, lithography and etching on oxidized silicon wafers. Suitable techniques include those disclosed in the following references, which are incorporated herein by reference in their entirety:

Park, H., et al., *Applied Physics Letters,* 75: 301-303 (1999);

Zhou, C., et al., *Applied Physics Letters,* 67: 1160-1162 (1995);

Bezryadin, A. and C. Dekker, *Journal of Vacuum Science & Technology B: Microelectronics and Nanometer Structures,* 15: 793-799 (1997); and Bezryadin, A., C. Dekker, and G. Schmid, *Applied Physics Letters,* 71: 1273-1275 (1997).

Fabrication of controlled nano-gap electrodes is another efficient method of trapping the oligonucleotide probes. This method also follows the same procedure of integrating single or double strand DNA into a circuit using metal electrodes to perform conductivity measurements. The separation between the electrodes must be small in accordance with the length nucleic acid molecules used.

In certain embodiments, a 7-bit addressing scheme with multiplexer circuits may be used in conjunction with an analog signal for the biasing of the sensing/measurement block at the nanogap. An external clock may be used on the mounting printed circuit board to provide the measurement frequency. The clock enables the input biasing across the sensing/measurement block. The current or conductance in response to the bias is measured at the shared output electrode and may be normalized and co-related with the preceding and following data gathered from the same sensing/measurement block.

In certain embodiments, the invention is directed to methods of forming a metallic nano-scale break junction on a chip, comprising:

forming on said chip a metal line, preferably having a thickness of less than about 5 µm and a width less than about 5 µm;

bombarding said metal line with a focused-ion beam to form a thinned section in said metal line; and applying current to said metal line sufficient to cause electromigration in said thinned section of said metal line.

In preferred embodiments, the metal line is formed using photolithography.

Probes

The probes used in the devices, systems, and methods of the invention are hairpin loop oligonucleotides. The hairpin loop oligonucleotides unwinds only in the presence of single-stranded oligonucleotide target complementary to loop region or at least one arm of the double-stranded stem region (one arm remains attached to the substrate via the optional linker and the other arm becomes the unattached tail when the hairpin loop opens). In certain embodiments, the oligonucleotide probes are covalently attached to said substrate.

In one embodiment, the oligonucleotide probes are amine-modified to permit covalent attachment to the substrate. In certain embodiments, there is direct attachment of the oligonucleotide probe through a silane, such as, for example, (3-glycidyloxypropyl)trimethoxysilane). In other embodiments, there is attachment through a homo-bifunctional layer, such as, for example, 1,4-phenylene diisothiocyanate, on top of a silane, such as, for example, 3-aminopropyltrimethoxysilane.

In certain embodiments, each of said first oligonucleotide probes comprise:

an optional spacer having about one nucleotide base to about 20 nucleotide bases;

a nucleotide loop having about 3 nucleotide bases to about 100 nucleotide bases; and a base pair stem having about 3 nucleotide base pairs to about 20 nucleotide base pairs.

In certain embodiments, each of said first oligonucleotide probes comprise:

a spacer having about 3 nucleotide bases;

a nucleotide loop having about 12 nucleotide bases; and a base pair stem having about 6 nucleotide base pairs.

Oligonucleotides of defined sequences are used for a variety of purposes in the practice of the invention. Methods of making oligonucleotides of a predetermined sequence are well-known. See, e.g., Sambrook et al., *Molecular Cloning: A Laboratory Manual* (2nd ed. 1989) and F. Eckstein (ed.) *Oligonucleotides and Analogues,* 1st Ed. (Oxford University Press, New York, 1991). Solid-phase synthesis methods are preferred for both oligoribonucleotides and oligodeoxyribonucleotides (the well-known methods of synthesizing DNA are also useful for synthesizing RNA). Oligoribonucleotides and oligodeoxyribonucleotides can also be prepared enzymatically.

The selection of probes and their organization in an array depends upon the use to which the biological chip will be put. In one embodiment, the chips are used to sequence or re-sequence nucleic acid molecules, or compare their sequence to a reference molecule. Re-sequencing nucleic acid molecules involves determining whether a particular molecule has any deviations from the sequence of reference molecule.

In typical diagnostic applications, a solution containing one or more targets to be identified (i.e., samples from patients) contacts the probe array. The targets will bind or hybridize with complementary probe sequences. Accordingly, the probes will be selected to have sequences directed to (i.e., having at least some complementarity with) the target sequences to be detected, e.g., human or pathogen sequences. The nanoparticle reporter conjugates only hybridize with those probes where there has been a binding event with a target, permitting an electrical current to be detected at known locations. Accordingly, locations at which targets hybridize with complimentary probes can be identified by locating the electrical current in an electrode set. Based on the locations of the electrodes where hybridization occurs, information regarding the target sequences can be extracted. The existence of a mutation may be determined by comparing the target sequence with the wild type.

Individual probe sequence may be designed to detect known single nucleotide base mutations, such as, for example, the K-ras mutation described in the examples, which is a prognostic indicator for lung cancer, other cancers, cystic fibrosis, and sickle cell anemia. However, the invention is not limited to methods of detecting known single nucleotide base mutations, but may be used to identify the nucleic acid sequence of any desired target.

The hairpin loop oligonucleotide probes may be immobilized on the substrate between the electrodes using the surface chemistry described by the techniques described in M. Manning, S. Harvey, P. Galvin, and G. Redmond, *Materials Science and Engineering*, C 23, 347 (2003), incorporated herein by reference.

In certain embodiments, oligonucleotide probes form a self-assembled monolayer between the electrodes.

The oligonucleotide probes may be directed to and located in the gaps between a particular set(s) of electrodes by electrostatic trapping, i.e., energizing a particular set(s) of electrodes, preferably using alternating current, to direct the probes (which are charged) to the gaps. Different oligonucleotide probes, referred herein as "second oligonucleotide probes," may be localized at their respective electrodes by providing the second oligonucleotide probes and sequentially energizing the desired set(s) of electrodes to direct and localize the second oligonucleotide probes in the appropriate nanogap(s). This procedure may be repeated until all of the different oligonucleotide probes are directed to and located in the nanogap(s) between their desired set(s) of electrodes.

Microfluidic Channels

Assays on biological arrays generally include contacting a probe array with a sample under the selected reaction conditions, optionally washing the well to remove unreacted molecules, and analyzing the biological array for evidence of reaction between target molecules and the probe molecules. These steps involve handling fluids. Microfluidic channels 15 may be used to deliver the liquids to the test sites, such as the one shown in FIG. 14 made from any suitable solid material, such as polydimethylsiloxane. The methods of this invention automate these steps so as to allow multiple assays to be performed concurrently. Accordingly, this invention employs automated fluid handling systems for concurrently performing the assay steps in each of the test wells. Fluid handling allows uniform treatment of samples in the test sites. Microtiter robotic and fluid-handling devices are available commercially, for example, from Tecan AG.

The device may be introduced into a holder in the fluid-handling device. This robotic device may be programmed to set appropriate reaction conditions, such as temperature, add samples to the device, incubate the test samples for an appropriate time, remove unreacted samples, wash the wells, add substrates as appropriate and perform detection assays. The particulars of the reaction conditions depend upon the purpose of the assay. For example, in a sequencing assay involving DNA hybridization, standard hybridization conditions are chosen. However, the assay may involve testing whether a sample contains target molecules that react to a probe under a specified set of reaction conditions. In this case, the reaction conditions are chosen accordingly.

Systems

In other aspects, the invention is directed to systems, comprising:

a device described herein; and a plurality of nanoparticle reporter conjugates;

wherein said nanoparticle reporter conjugates comprise at least one nanoparticle and a single-stranded oligonucleotide complementary to at least a portion of said stem of said first oligonucleotide probe; and wherein said nanoparticle in said nanoparticle reporter conjugate is a metal, semiconductor, or magnetic colloidal particle;

In certain embodiments of the system, said single-stranded oligonucleotide complementary to at least a portion of said stem of said hairpin loop probe comprises about 3 nucleotide bases to about 80 nucleotide bases. In certain embodiments of the system, said single-stranded oligonucleotide complementary to at least a portion of said stem of said hairpin loop probe comprises about 7 nucleotide bases. In certain preferred embodiments, the single-stranded oligonucleotide is complementary to the strand of the stem region of the hairpin loop that is attached to the optional spacer and substrate. In other embodiments, the single-stranded oligonucleotide is complementary to the strand of the stem region of the hairpin loop that becomes the unattached tail of probe.

In other aspects, the invention is directed to systems, comprising:

a multiplexing device described herein; and a plurality of first nanoparticle reporter conjugates; and a plurality of at least one second nanoparticle reporter conjugates;

wherein said first nanoparticle reporter conjugates comprise at least one nanoparticle and a single-stranded oligonucleotide complementary to at least a portion of said stem of said first oligonucleotide probes;

wherein said nanoparticle in said first nanoparticle reporter conjugate is a metal, semiconductor, or magnetic colloidal particle;

wherein said second nanoparticle reporter conjugates comprise at least one nanoparticle and a single-stranded oligonucleotide complementary to at least a portion of said stem of said second oligonucleotide probes;

wherein said nanoparticle in said second nanoparticle reporter conjugate is a metal, semiconductor, or magnetic colloidal particle;

wherein said second nanoparticle reporter conjugates are the same or different from said first nanoparticle reporter conjugates; and wherein said second nanoparticle reporter conjugates are the same or different from said other second nanoparticle reporter conjugates.

In certain embodiments of the system, said single-stranded oligonucleotide complementary to at least a portion of said stem of said hairpin loop probe comprises about 3 nucleotide bases to about 80 nucleotide bases. In certain embodiments of the system, said single-stranded oligonucleotide complementary to at least a portion of said stem of said hairpin loop probe comprises about 7 nucleotide bases.

In further embodiments, the systems further comprising:

an electrical reading device for interrogating said device described herein.

In certain preferred embodiments, said electrical reading device is portable.

Nanoparticle Reporter Conjugates

The nanoparticle reporter conjugates of the invention comprise at least one nanoparticle (either a metal, semiconductor, or magnetic colloidal particle) and a single-stranded oligonucleotide complementary to at least a portion of said stem of said oligonucleotide probe. In certain embodiments, the nanoparticle reporter conjugates further comprise a linker. While not wishing to be bound by theory, it is believed that the nanoparticle reporter conjugates hybridize with the exposed stem portion of the hairpin loop probes attached in the nanogap of the electrodes. This hybridization facilitates the movement of electrons, at least partially due to the $\pi$-stacking of base pairs of the nucleic acids in the double helix structure, thereby increasing the charge conduction between the electrodes. The melting and hybridization of the hairpin loop oligonucleotide with perfectly complementary targets and subsequently with the nanoparticle reporter conjugates permits charge transport, thus making electrical detection possible.

Nanoparticles useful in the practice of the invention include metal (e.g., gold, silver, copper and platinum), semiconductor (e.g., CdSe, CdS, and CdS or CdSe coated with ZnS) and magnetic (e.g., ferromagnetite) colloidal materials. In certain embodiments, metal nanoparticles, especially gold nanoparticles, are preferred. The use of semiconductor and magnetic particles permits the use of the same system for multi-modal detection, including capacitance change, impedance change, or from field effect, for example. Other nanoparticles useful in the practice of the invention include ZnS, ZnO, $TiO_2$, AgI, AgBr, $HgI_2$, PbS, PbSe, ZnTe, CdTe, $In_2S_3$, $In_2Se_3$, $Cd_3P_2$, $Cd_3As_2$, InAs, and GaAs. The size of the nanoparticles is preferably from about 5 nm to about 150 nm (mean diameter), more preferably from about 5 to about 50 nm, most preferably from about 10 to about 30 nm. The nanoparticles may also be rods.

Methods of making metal, semiconductor and magnetic nanoparticles are well-known in the art. See, e.g., Schmid, G. (ed.) *Clusters and Colloids* (VCH, Weinheim, 1994); Hayat, M. A. (ed.) *Colloidal Gold: Principles, Methods, and Applications* (Academic Press, San Diego, 1991); Massart, R., *IEEE Transactions On Magnetics*, 17, 1247 (1981); Ahmadi, T. S. et al., *Science*, 272, 1924 (1996); Henglein, A. et al., *J. Phys. Chem.*, 99, 14129 (1995); Curtis, A. C., et al., *Angew. Chem. Int. Ed. Engl.*, 27, 1530 (1988), all of which are incorporated herein by reference.

Methods of making ZnS, ZnO, $TiO_2$, AgI, AgBr, $HgI_2$, PbS, PbSe, ZnTe, CdTe, $In_2S_3$, $In_2Se_3$, $Cd_3P_2$, $Cd_3As_2$, InAs, and GaAs nanoparticles are also known in the art. See, e.g., Weller, *Angew. Chem. Int. Ed. Engl.*, 32, 41 (1993); Henglein, *Top. Curr. Chem.*, 143, 113 (1988); Henglein, *Chem. Rev.*, 89, 1861 (1989); Brus, *Appl. Phys. A.*, 53, 465 (1991); Bahncmann, in *Photochemical Conversion and Storage of Solar Energy* (eds. Pelizetti and Schiavello 1991), page 251; Wang and Herron, *J. Phys. Chem.*, 95, 525 (1991); Olshaysky et al., *J. Am. Chem. Soc.*, 112, 9438 (1990); Ushida et al., *J. Phys. Chem.*, 95, 5382 (1992), all of which are incorporated herein by reference.

Suitable nanoparticles are also commercially available from, e.g., Ted Pella, Inc. (gold), Amersham Corporation (gold) and Nanoprobes, Inc. (gold).

Presently preferred for use in detecting nucleic acids are gold nanoparticles because of their stability, ease of imaging by electron microscopy, and well-characterized modification with thiol functionalities.

The nanoparticles, the oligonucleotides, or both are functionalized in order to attach the oligonucleotides to the nanoparticles. Such methods are known in the art. For instance, oligonucleotides functionalized with alkanethiols at their 3'-termini or 5'-termini readily attach to gold nanoparticles. See Whitesides, *Proceedings of the Robert A. Welch Foundation 39th Conference On Chemical Research Nanophase Chemistry*, Houston, Tex., pages 109-121 (1995). See also, Mucic et al., *Chem. Commun.* 555-557 (1996), which describes a method of attaching 3' thiol DNA to flat gold surfaces; this method can be used to attach oligonucleotides to nanoparticles. The alkanethiol method can also be used to attach oligonucleotides to other metal, semiconductor, and magnetic colloids and to the other nanoparticles listed above. Other functional groups for attaching oligonucleotides to solid surfaces include phosphorothioate groups (see, e.g., U.S. Pat. No. 5,472,881 for the binding of oligonucleotide-phosphorothioates to gold surfaces), substituted alkylsiloxanes (see, e.g. Burwell, *Chemical Technology*, 4, 370-377 (1974) and Matteucci and Caruthers, *J. Am. Chem. Soc.*, 103, 3185-3191 (1981) for binding of oligonucleotides to silica and glass surfaces, and Grabar et al., *Anal. Chem.*, 67, 735-743 for binding of aminoalkylsiloxanes and for similar binding of mercaptoaklylsiloxanes). Oligonucleotides terminated with a 5' thionucleoside or a 3' thionucleoside may also be used for attaching oligonucleotides to solid surfaces. The following references describe other methods that may be employed to attached oligonucleotides to nanoparticles: Nuzzo et al., *J. Am. Chem. Soc.*, 109, 2358 (1987) (disulfides on gold); Allara and Nuzzo, *Langmuir*, 1, 45 (1985) (carboxylic acids on aluminum); Allara and Tompkins, *J. Colloid Interface Sci.*, 49, 410-421 (1974) (carboxylic acids on copper); Iler, *The Chemistry Of Silica*, Chapter 6, (Wiley 1979) (carboxylic acids on silica); Timmons and Zisman, *J. Phys. Chem.*, 69, 984-990 (1965) (carboxylic acids on platinum); Soriaga and Hubbard, *J. Am. Chem. Soc.*, 104, 3937 (1982) (aromatic ring compounds on platinum); Hubbard, *Acc. Chem. Res.*, 13, 177 (1980) (sulfolanes, sulfoxides and other functionalized solvents on platinum); Hickman et al., *J. Am. Chem. Soc.*, 111, 7271 (1989) (isonitriles on platinum); Maoz and Sagiv, *Langmuir*, 3, 1045 (1987) (silanes on silica); Maoz and Sagiv, *Langmuir*, 3, 1034 (1987) (silanes on silica);

Wasserman, et al., *Langmuir*, 5, 1074 (1989) (silanes on silica); Eltekova and Eltekov, *Langmuir*, 3, 951 (1987) (aromatic carboxylic acids, aldehydes, alcohols and methoxy groups on titanium dioxide and silica); Lec, et al., *J. Phys. Chem.*, 92, 2597 (1988) (rigid phosphates on metals).

Oligonucleotides functionalized with a cyclic disulfide are within the scope of this invention. The cyclic disulfides preferably have 5 or 6 atoms in their rings, including the two sulfur atoms. Suitable cyclic disulfides are available commercially or may be synthesized by known procedures. The reduced form of the cyclic disulfides can also be used.

Preferably, the optional linker further comprises a hydrocarbon moiety attached to the cyclic disulfide. Suitable hydrocarbons are available commercially, and are attached to the cyclic disulfides. Preferably the hydrocarbon moiety is a steroid residue. Oligonucleotide-nanoparticle conjugates prepared using linkers comprising a steroid residue attached to a cyclic disulfide are stable to thiols (e.g., dithiothreitol used in polymerase chain reaction (PCR) solutions) as compared to conjugates prepared using alkanethiols or acyclic disulfides as the linker. This stability is likely due to the fact that each oligonucleotide is anchored to a nanoparticle through two sulfur atoms, rather than a single sulfur atom. In particular, it is thought that two adjacent sulfur atoms of a cyclic disulfide would have a chelation effect which would be advantageous in stabilizing the oligonucleotide-nanoparticle conjugates. The large hydrophobic steroid residues of the linkers contribute to the stability of the conjugates by screening the nanoparticles from the approach of water-soluble molecules to the surfaces of the nanoparticles.

In view of the foregoing, the two sulfur atoms of the cyclic disulfide should preferably be close enough together so that both of the sulfur atoms can attach simultaneously to the nanoparticle. Most preferably, the two sulfur atoms are adjacent each other. Also, the hydrocarbon moiety should be large so as to present a large hydrophobic surface screening the surfaces of the nanoparticles.

Electrical Reader

Suitable electrical reading devices include any device for low power printed circuit board electronics capable of measuring either sequentially or in parallel a small change in conductivity, resistivity, capacitance, or impedance in a picoampere range. The Agilent 4155C semiconductor parameter analyzer and the Agilent 4156C semiconductor parameter analyzer are examples of suitable devices.

Methods

The invention provides a nanotechnology-based low-power, rapid, inexpensive, recyclable, and sensitive electrical detection device, system, and method of sub-femtomolar concentrations of nucleic acids, including genes, with no external sample preparation or labeling or other chemical modification of the sample. The biosensors of the invention may be used in wide variety of applications requiring sensitive nucleic acid detection, including, but not limited to, forensics, early disease detection, disease progression monitoring (such as in response to therapy and/or medicinal agents), legal matters (such as paternity and criminal proceedings), defensive biohazard detection, and immigration issues (such as establishing blood relationships). The biosensors of the invention are useful in further enabling "personalized medicine," where drugs are designed according to each individual's genetic make-up.

In another aspect, the invention is directed to methods for detecting nucleic acid hybridization, comprising:

providing a device, comprising:
a thermally responsive, electrically insulating substrate;
at least one heating element; and
a first detecting unit, comprising:
a first electrode and a second electrode separated by a nanogap; and
a plurality of first oligonucleotide probes attached to said substrate in said nanogap;
wherein said first oligonucleotide probes are in a hairpin loop formation and have the same nucleic acid sequence; and
wherein said first oligonucleotide probes comprise an optional spacer, a loop, and a stem region, said stem region being double-stranded;
providing a solution comprising at least one buffer and single-stranded oligonucleotide target under hybridizing conditions;
wherein said single-stranded oligonucleotide target hybridizes at least some of said oligonucleotide probes to form elongated oligonucleotide probes;
providing a plurality of first nanoparticle reporter conjugates under hybridizing conditions;
wherein said first nanoparticle reporter conjugates comprise at least one nanoparticle and an oligonucleotide complementary to at least a portion of said stem of said first oligonucleotide probes;
applying a voltage drop across said electrodes; and
measuring a change in conductivity, resistivity, capacitance, or impedance across said electrodes at known locations to determine perfect complementarity of said oligonucleotide target to said first oligonucleotide probes.

In certain embodiments, the methods further comprise:
washing to remove unhybridized components from said detecting unit.

In certain embodiments, the methods further comprise:
heating said device to remove said hybridized targets and said hybridized nanoparticle reporter conjugates from said probe to permit recycling of said detecting unit.

In certain embodiments, the methods further comprise:
heating a solution comprising double stranded oligonucleotide target to form said solution comprising single-stranded oligonucleotide target.

In certain embodiments, the methods further comprise:
forming a temperature gradient to focus said single stranded oligonucleotide target at said detecting unit.

In certain embodiments, the methods further comprise:
reversing the polarity of said voltage drop to remove unbound components or nonspecifically bound components from said detecting unit.

The methods of the invention may be used to quantify the level of oligonucleotides or polypeptides. For example, the change in conductance (or other electrical characteristic) between nanogaps is direct function of the number of nanoparticles located between nanogaps. The number of nanoparticles is a direct function of the number of perfectly complementary oligonucleotides that have hybridized. Thus, the change of conductivity (or other electrical characteristic) can be directly correlated to the quantity of perfectly complementary oligonucleotides or polypeptides present in the sample.

In certain embodiments, the methods further comprise:
providing, in addition to said first detecting unit, a plurality of additional detecting units, each additional detecting unit comprising:
a first electrode and a second electrode separated by a nanogap; and
a plurality of second oligonucleotide probes attached to said substrate in said nanogap;
wherein said second oligonucleotide probes are in a hairpin loop formation and have the same nucleic acid sequence; and wherein said second oligonucleotide probes comprise an optional spacer, a loop, and a stem region, said stem region being double-stranded;

wherein said second oligonucleotide probes are the same or different from said first oligonucleotides in said first detecting unit; and wherein said second oligonucleotide probes are the same or different from other second oligonucleotide probes in said plurality of second detecting units;

providing a plurality of at least one second nanoparticle reporter conjugates under hybridizing conditions;

wherein said second nanoparticle reporter conjugates comprise at least one nanoparticle and an oligonucleotide complementary to at least a portion of said stem of said second oligonucleotide probes;

wherein said second nanoparticle reporter conjugates are the same or different from said first nanoparticle reporter conjugates;

wherein said second nanoparticle reporter conjugates are the same or different from said other second nanoparticle reporter conjugates;

wherein said measuring step is carried out in parallel or sequentially for said first detecting unit and said plurality of said additional detecting units.

In certain embodiments, said voltage drop is applied as direct current. In other embodiments, said voltage drop is applied as alternating current and the alternating current impedance measured.

In certain embodiments, said measuring step measures an increase in conductivity across said electrodes at known locations to determine perfect complementarity of said oligonucleotide target to said first oligonucleotide probes.

In certain embodiments, said single-stranded oligonucleotide target is prepared by heating a solution comprising double-stranded oligonucleotide target.

In certain embodiments, the invention is directed to methods for detecting nucleic acid hybridization, comprising:

providing a device, comprising:
a thermally responsive, electrically insulating substrate;
at least one heating element; and
a first detecting unit, comprising:
a first electrode and a second electrode separated by a nanogap; and
a plurality of first oligonucleotide probes attached to said substrate in said nanogap;
wherein said first oligonucleotide probes are in a hairpin loop formation and have the same nucleic acid sequence; and
wherein said first oligonucleotide probes comprise an optional spacer, a loop, and a stem region, said stem region being double-stranded;

providing a solution comprising at least one buffer and single-stranded oligonucleotide target under hybridizing conditions;

wherein said single-stranded oligonucleotide target hybridizes at least some of said oligonucleotide probes to form elongated oligonucleotide probes;

providing a plurality of first reporter conjugates under hybridizing conditions;

wherein said first reporter conjugates comprise an oligonucleotide complementary to at least a portion of said stem of said first oligonucleotide probes;

reversibly exchanging an imino proton in each base pair of said first reporter conjugate or said stem of said first oligonucleotide probes with a metal ion selected from the group consisting of gold ion, silver ion, platinum ion, and copper ion;

applying a voltage drop across said electrodes; and measuring a change in conductivity, resistivity, capacitance, or impedance across said electrodes at known locations to determine perfect complementarity of said oligonucleotide target to said first oligonucleotide probes.

The reversible exchanging of an imino proton in each base pair may be carried out as described in A. Rakitin, Aich, P., Papadopoulos, C., Kobzar, Yu., Vedeneev, A. S., Lee, J. S., J. M. Xu, *Phys. Rev. Lett.*, 86(16), 3670-3673, (2001), which is incorporated herein by reference. Certain embodiments of this method, where there is multiplexing of the detecting units, further comprise the steps of:

providing, in addition to said first detecting unit, a plurality of additional detecting units, each additional detecting unit comprising:
a first electrode and a second electrode separated by a nanogap; and
a plurality of second oligonucleotide probes attached to said substrate in said nanogap;
wherein said second oligonucleotide probes are in a hairpin loop formation and have the same nucleic acid sequence; and
wherein said second oligonucleotide probes comprise an optional spacer, a loop, and a stem region, said stem region being double-stranded;
wherein said second oligonucleotide probes are the same or different from said first oligonucleotides in said first detecting unit; and
wherein said second oligonucleotide probes are the same or different from other second oligonucleotide probes in said plurality of second detecting units;

providing a plurality of at least one second reporter conjugates under hybridizing conditions;

wherein said second reporter conjugates comprise an oligonucleotide complementary to at least a portion of said stem of said second oligonucleotide probes;

wherein said second reporter conjugates are the same or different from said first nanoparticle reporter conjugates;

wherein said second reporter conjugates are the same or different from said other second nanoparticle reporter conjugates;

reversibly exchanging an imino proton in each base pair of said second reporter conjugate or said stem of said second oligonucleotide probes with a metal ion selected from the group consisting of gold ion, silver ion, platinum ion, and copper ion;

wherein said measuring step is carried out in parallel or sequentially for said first detecting unit and said plurality of said additional detecting units.

In certain embodiments of this method, said voltage drop is applied as direct current. In other embodiments, said voltage drop is applied as alternating current and the alternating current impedance measured. In certain embodiments, said measuring step measures an increase in conductivity across said electrodes at known locations to determine perfect complementarity of said oligonucleotide target to said first oligonucleotide probes. In certain embodiments, said single-stranded oligonucleotide target is prepared by heating a solution comprising double-stranded oligonucleotide target.

In certain embodiments, the invention is directed to methods for detecting nucleic acid hybridization, comprising:

providing a device, comprising:
a thermally responsive, electrically insulating substrate;
at least one heating element; and
a first detecting unit, comprising:
a first electrode and a second electrode separated by a nanogap; and a plurality of first oligonucleotide probes attached to said substrate in said nanogap;
wherein said first oligonucleotide probes are in a hairpin loop formation and have the same nucleic acid sequence; and
wherein said first oligonucleotide probes comprise an optional spacer, a loop, and a stem region, said stem region being double-stranded;
providing a solution comprising at least one buffer and single-stranded oligonucleotide target under hybridizing conditions;
wherein said single-stranded oligonucleotide target hybridizes at least some of said oligonucleotide probes to form elongated oligonucleotide probes;
providing a plurality of first nanoparticle reporter conjugates under hybridizing conditions to form a double stranded nucleic acid sequence;
wherein said first nanoparticle reporter conjugates comprise an oligonucleotide complementary to at least a portion of said stem of said first oligonucleotide probes;
vectorially depositing silver on said double stranded nucleic acid sequence;
applying a voltage drop across said electrodes; and
measuring a change in conductivity, resistivity, capacitance, or impedance across said electrodes at known locations to determine perfect complementarity of said oligonucleotide target to said first oligonucleotide probes.

In certain embodiments of this method, the vectorially depositing step comprises:
ion exchanging silver ions on said double stranded nucleic acid sequence;
reducing said silver ions; and
developing silver aggregates on said double stranded nucleic acid sequence; as described in E. Braun, Y. Eichen, U. Sivan, and G. Ben-Yoseph, *Nature,* 391(6669), 775-778, (1998), incorporated herein by reference. Certain embodiments of this method, where there is multiplexing of the detecting units, further comprise the steps of:
providing, in addition to said first detecting unit, a plurality of additional detecting units, each additional detecting unit comprising:
a first electrode and a second electrode separated by a nanogap; and
a plurality of second oligonucleotide probes attached to said substrate in said nanogap;
wherein said second oligonucleotide probes are in a hairpin loop formation and have the same nucleic acid sequence; and
wherein said second oligonucleotide probes comprise an optional spacer, a loop, and a stem region, said stem region being double-stranded;
wherein said second oligonucleotide probes are the same or different from said first oligonucleotides in said first detecting unit; and
wherein said second oligonucleotide probes are the same or different from other second oligonucleotide probes in said plurality of second detecting units;
providing a plurality of at least one second reporter conjugates under hybridizing conditions;
wherein said second reporter conjugates comprise an oligonucleotide complementary to at least a portion of said stem of said second oligonucleotide probes;
wherein said second reporter conjugates are the same or different from said first nanoparticle reporter conjugates;
wherein said second reporter conjugates are the same or different from said other second nanoparticle reporter conjugates; and
vectorially depositing silver on said double stranded nucleic acid sequence;
wherein said measuring step is carried out in parallel or sequentially for said first detecting unit and said plurality of said additional detecting units.

In certain embodiments of this method, said voltage drop is applied as direct current. In other embodiments, said voltage drop is applied as alternating current and the alternating current impedance measured. In certain embodiments, said measuring step measures an increase in conductivity across said electrodes at known locations to determine perfect complementarity of said oligonucleotide target to said first oligonucleotide probes. In certain embodiments, said single-stranded oligonucleotide target is prepared by heating a solution comprising double-stranded oligonucleotide target.

In certain embodiments, the invention is directed to methods for detecting nucleic acid hybridization, comprising:
providing a device, comprising:
a thermally responsive, electrically insulating substrate;
at least one heating element; and
a first detecting unit, comprising:
a first electrode and a second electrode separated by a nanogap; and
a plurality of first oligonucleotide probes attached to said substrate in said nanogap;
wherein said first oligonucleotide probes are in a hairpin loop formation and have the same nucleic acid sequence; and
wherein said first oligonucleotide probes comprise an optional spacer, a loop, and a stem region, said stem region being double-stranded;
providing a solution comprising at least one buffer and single-stranded oligonucleotide target under hybridizing conditions;
wherein said single-stranded oligonucleotide target hybridizes at least some of said first oligonucleotide probes to form elongated oligonucleotide probes;
providing a plurality of first reporter molecules under hybridizing conditions to form a double stranded oligonucleotide-stem complex;
wherein said first reporter molecules comprise an oligonucleotide complementary to at least a portion of said stem of said first oligonucleotide probes;
providing a solution comprising first nanoparticle polypeptide conjugates;
wherein said first nanoparticle polypeptide conjugates comprise at least one nanoparticle and a polypeptide, preferably comprising at least one residue of cysteine, that binds to said double stranded oligonucleotide-stem complex;
wherein said nanoparticle in said first nanoparticle polypeptide conjugates is a metal, semiconductor, or magnetic colloidal particle;
applying a voltage drop across said electrodes; and
measuring a change in conductivity, resistivity, capacitance, or impedance across said electrodes at known locations to determine perfect complementarity of said oligonucleotide target to said first oligonucleotide probes. The nanoparticle polypeptide conjugates, when hybridized to the stem section of the opened hairpin loop, provide the conduction paten for electrical detection of hybridization between the target and probe. In further embodiment, this method, where there is multiplexing of detecting devices, further comprises:
providing, in addition to said first detecting unit, a plurality of additional detecting units, each additional detecting unit comprising:
a first electrode and a second electrode separated by a nanogap; and a plurality of second oligonucleotide probes attached to said substrate in said nanogap;

wherein said second oligonucleotide probes are in a hairpin loop formation and have the same nucleic acid sequence;

wherein said second oligonucleotide probes comprise an optional spacer, a loop, and a stem region, said stem region being double-stranded;

wherein said second oligonucleotide probes are the same or different from said first oligonucleotides in said first detecting unit; and wherein said second oligonucleotide probes are the same or different from other second oligonucleotide probes in said plurality of second detecting units;

providing a plurality of second reporter molecules under hybridizing conditions to form a double stranded oligonucleotide-stem complex;

wherein said second reporter molecules comprise an oligonucleotide complementary to at least a portion of said stem of said second oligonucleotide probes;

providing a solution comprising second nanoparticle polypeptide conjugates;

wherein said second nanoparticle polypeptide conjugates comprise at least one nanoparticle and a polypeptide, preferably comprising at least one residue of cysteine, that binds to said double stranded oligonucleotide-stem complex;

wherein said nanoparticle in said second nanoparticle polypeptide conjugates is a metal, semiconductor, or magnetic colloidal particle;

wherein said second reporter molecules are the same or different from said first reporter molecules;

wherein said second reporter molecules are the same or different from other second reporter molecules;

wherein said measuring step is carried out in parallel or sequentially for said first detecting unit and said plurality of said additional detecting units.

In certain embodiments of this method, said voltage drop is applied as direct current. In other embodiments, said voltage drop is applied as alternating current and the alternating current impedance measured. In certain embodiments, said measuring step measures an increase in conductivity across said electrodes at known locations to determine perfect complementarity of said oligonucleotide target to said first oligonucleotide probes. In certain embodiments, said single-stranded oligonucleotide target is prepared by heating a solution comprising double-stranded oligonucleotide target.

The methods of this invention will find particular use wherever high through-put of samples is required. In particular, this invention is useful in clinical settings and for sequencing large quantities of DNA, RNA, or protein, especially at low concentrations in the femtomolar range.

The clinical setting requires performing the same test on many patient samples. The automated methods of this invention lend themselves to these uses when the test is one appropriately performed on a biological chip. For example, a DNA array can determine the particular strain of a pathogenic organism based on characteristic DNA sequences of the strain. The advanced techniques based on these assays now can be introduced into the clinic. Fluid samples from several patients are introduced into the test wells of a biological chip plate and the assays are performed concurrently.

In some embodiments, it may be desirable to perform multiple tests on multiple patient samples concurrently. According to such embodiments, rows (or columns) of the microtiter plate will contain probe arrays for diagnosis of a particular disease or trait. For example, one row might contain probe arrays designed for a particular cancer, while other rows contain probe arrays for another cancer. Patient samples are then introduced into respective columns (or rows) of the microtiter plate. For example, one column may be used to introduce samples from patient "one," another column for patient "two" etc. Accordingly, multiple diagnostic tests may be performed on multiple patients in parallel. In still further embodiments, multiple patient samples are introduced into a single well. In a particular well indicator the presence of a genetic disease or other characteristic, each patient sample is then individually processed to identify which patient exhibits that disease or trait. For relatively rarely occurring characteristics, further order-of-magnitude efficiency may be obtained according to this embodiment.

Particular assays that will find use in automation include those designed specifically to detect or identify particular variants of a pathogenic organism, such as HIV. Assays to detect or identify a human or animal gene are also contemplated. In one embodiment, the assay is the detection of a human gene variant that indicates existence of or predisposition to a genetic disease, either from acquired or inherited mutations in an individual DNA. These include genetic diseases such as cystic fibrosis, diabetes, and muscular dystrophy, as well as diseases such as cancer (the P53 gene is relevant to some cancers), as disclosed in U.S. Pat. No. 5,837,832.

It will be apparent to those skilled in the art that various modifications and variations can be made in the present invention and specific examples provided herein without departing from the spirit or scope of the invention. Thus, it is intended that the present invention cover the modifications and variations of this invention that come within the scope of any claims and their equivalents.

EXAMPLES

The present invention is further defined in the following Examples, in which all parts and percentages are by weight and degrees are Celsius, unless otherwise stated. It should be understood that these examples, while indicating preferred embodiments of the invention, are given by way of illustration only. From the above discussion and these examples, one skilled in the art can ascertain the essential characteristics of this invention, and without departing from the spirit and scope thereof, can make various changes and modifications of the invention to adapt it to various usages and conditions.

Example 1

A two-step photolithography process was used to achieve the structures on a thermally oxidized silicon wafer. In the first step of photolithography, a 3 μm wide line pattern was defined and e-beam evaporation of 50 Å of titanium (as sticky layer) and 150 Å of gold was done (FIG. 15). Lift-off created the metal lines on the wafer. The second optical lithography was done to pattern probing pads aligned to the metal lines. The probing pads were made of 100 Å titanium and 500 Å gold.

In this example, a manual focused-ion beam (FIB) milling process was performed on metal lines to make a scratch on the surface of the metal. A 30 KV acceleration voltage was used for the FIB scratching using gallium ions. A number of characterization runs were carried out to ensure that FIB does not remove all of the metal line during scratching.

The FIB based partial scratching of the metal lines creates controlled nano-gaps for break junction fabrication. This ensures a minimal footprint FIB process as compared to patterning the whole line using e-beam writing. An advantage stems from a parametric study that does not require the need of e-beam-written alignment marks or the definition of complete patterns for metallic break junctions.

The current-voltage (I-V) characteristics across the metal lines were measured using an Agilent I-V probe station, by applying a sweeping voltage and measuring the current flow in response. The I-V measurements were done before and after the FIB scratch, and again before and after the creation of break junction with electromigration.

After the chip was fabricated FIB scratching process was done on the chip. FIGS. 16A to 16C shows different FIB conditions that resulted in scratching of the gold lines. The amount of material removed from the metal lines was a direct function of the milling current and time of the process. A longer FIB exposure with higher milling current resulted in complete removal of the material from a wide area (FIG. 16A). Reducing the milling current resulted in removal of relatively less material but long exposure time (120 seconds) still resulted in a wide trench (FIG. 16B). Reducing the exposure time to 60 sec and milling current to 1 pA provided the optimum removal of material (FIG. 16C) and subsequent devices were processed at these conditions.

The I-V data was recorded after FIB scratch of metal lines. All devices showed a linear ohmic trend depicting electrical and physical continuity of the metal lines (FIG. 17). To break the metal lines electromigration voltage sweep (0 to ~7 V) was applied. The sudden drop in current depicted complete break in the metal line (Inset to FIG. 17). The SEM micrographs also showed complete breaking of metal lines (FIG. 18). The I-V data comparison before and after the application of the electromigration voltage is shown in FIG. 19. The current flow became negligible and only non-characteristic noise could be measured once the break junctions were completely formed.

A sample of conductances through the break junctions is plotted in FIG. 20. The graph clearly shows that most electrodes with a nanogap distance of about 200-500 nm had a conductance only in the range of a few nS. The size distribution showed a peak around 200 nm gaps in the junctions. This data further demonstrates the complete breaking of the junction by the reported method.

The results presented show that the break junctions were formed and characterized at each step. The FIB scratching process provided a rapid method to create thinned parts in the metal lines, resulting in very high electrical bottleneck to the flow of charge carriers. The high resistance and defects of the thinned part provided spatially localized break in metal lines.

During the FIB process, as a result of the application of a high voltage, the incident ions striking the surface of the metal transfer their energy to the electrons and atoms and eject the atoms from the surface. The ions may also be penetrating the metal film displacing the atoms from their positions. Acceleration voltage plays a key role in these two competing processes.

The penetration of the ions also depends on the penetration depth or range of the ions $R_p$. At depth D inside the material, if Gaussian curve is fitted to the distribution of the ions, it has the form of the following equation:

$$\frac{\mathrm{Exp}[-D - R_p)^2 * (\Delta R_p)^2]}{2}$$

where $\Delta R_p$ is the Range Straggle. The ejection of atoms and the number of atoms ejected from the surface depend on the energy of the striking ions. The typical yield is 1-10 atoms/ion. The yield also depends on the incident angle between ion beam and normal to the surface. Yield increases with $1/\cos\theta$, where $\theta$ is the incident angle, as described by Gadgil, V. J., Tong, H. D., Cesa, Y., and Bennink, M. L., *Surface & Coatings Technology*, 203(17-18), 2436-2441 (2009). The milling is controlled by the milling current and time interval of the FIB process. We wanted to only scratch the surface of the metal line, not mill it, as milling could cause defects in underlying $SiO_2$ layer which needs to be maintained plain and viable for possible immobilization of probe molecules.

The electromigration is the phenomenon where the application of an external electric field causes a large current density in the wires. The electrons of the metal move under the influence of such fields; if a defect in the metal is encountered, the momentum of the electrons is transferred to the defect. Slowly, the momentum exchange becomes larger, resulting in the build-up of a force. This causes the atoms to move away from the defect culminating in the effective breakdown of the metal, as described in Strachan, D. R., Smith, D. E., Johnston, D. E., Park, T. H., Therien, M. J., Bonnell, D. A., and Johnson, A. T., *Applied Physics Letters*, 86: 043109 (2005). FIB scratching not only provides a high resistance spot on the line but it also introduces defects that directly aid in spatially localized break in the line. The method produces nanogaps on FIB-scratched metal lines which allows for high aerial throughput and high yield. A yield of nanoscale gaps greater than 60% was realized, as compared to previously reported yield of 10-20% (Park, H., Lim, A. K. L., Alivisatos, A. P., Park, J., and Mceuen, P. L., *Applied Physics Letters*, 75:301 (1999); Mahapatro, A. K., Ghosh, S., and Janes, D. B., 2006, *IEEE Transactions on Nanotechnology*, 5(3): 232-236 (2006); Park, J., Pasupathy, A. N., Goldsmith, J. L, Chang, C., Yaish, Y., Petta, J. R., Rinkoski, N Sethna, J. P., Abruña, H. D., and McEuen, P. L., *Nature*, 41.7(6890): 722-725 (2002)). When compared to the conventional nanogap formation using e-beam lithography, the use of a focused-ion beam to scratch the metal surface is faster and less expensive.

Example 2

The chips with nanoelectrodes were fabricated in two steps of lithography. On the first layer Ti/Au thickness 50/150 Å metal pads 500 nm apart were made using e-beam lithography and lift-off. In the second step, optical lithography was done to fabricate probing pads to contact the nanoelectrodes. Bare silicon chips were used to test the attachment and detection schemes prior to using nanoelectrode chips.

The chips were cleaned in oxygen plasma at 200 W in $Ar+O_2$ and Piranha solution, followed by surface attachment of probe DNA in a nitrogen glovebox with controlled ambience and temperature, as described in S. M. Iqbal, D. Akin, and R. Bashir, *Nat. Nanotechnol.*, 2, 243-8 (2007), incorporated herein by reference. The surface-attached probe molecules were heat cycled in TrisEDTA (TE) buffer three times to ensure all molecules formed hairpin loop structures. The gold nanoparticle reporter conjugates were prepared using thiol-gold chemistry, as described in J. J. Storhoff, R. Elghanian, R. C. Mucic, C. A. Mirkin, R. L. Letsinger, *J. Am. Chem. Soc.*, 120(9), 1959-1964 (1998), incorporated herein by reference. The functionalized chips were immersed in TE buffer pH 7.4 containing target DNA, either perfect-complementary (PC) target or single mismatched target at a concentration of 2 fmol/l for 24 hours at 40° C.

Electrodes with nanogaps were fabrication through electromigration by passing a large current through 100 nm wide and 150 nm thick gold film, as described in S. M. Iqbal, G. Balasundaram, S. Ghosh, D. E. Bergstrom, and R. Bashir, *Applied Physics Letters* 86, 153901 (2005), incorporated herein by reference. The current-voltage characteristics of conduction before and after nanogap formation were measured.

Four different custom-designed single stranded DNA molecules were purchased (Sigma-Aldrich, St. Louis, Mo.) and used in this example. As shown in Table 1 below, two 18 base pair sequences were designed to be different at 1 bp (marked in bold). The wild-type DNA (SEQ ID NO:3) is referred to as "MM," and mutated DNA sequence (SEQ ID NO:2) is referred to as "PC." The 24 base hairpin loop oligonucleotide probe was designed to be perfectly complementary to PC (the mutated DNA sequence (SEQ ID NO:2)). The probe (SEQ ID NO:1) is modified with amine at the 5'-end.

TABLE 1

| Sequence Name | Oligonucleotide (5' to 3') | Modification | GC Content |
|---|---|---|---|
| Probe Sequence | AAA GGC AAT TTC GCC GCC GCC ATT GCC (SEQ ID NO: 1) | 5' C12 amine | 59.3% |
| Perfectly Complementary (PC) | GGC AAT GGC GGC GGC GAA (SEQ ID NO: 2) | None | 72.2% |
| Single Base Mismatch (MM) | GGC AGT GGC GGC GGC GAA (SEQ ID NO: 3) | None | 77.8% |
| Nanoparticle reporter conjugates | TGC CTT T | 5' thiol | 42.9% |

Four different chip systems were prepared:
1: silane+gold nanoparticle reporter conjugate
2: silane+hairpin loop probes+perfectly complementary target+gold nanoparticle reporter conjugate
3: silane+hairpin loop probes+single base mismatched target+gold nanoparticle reporter conjugate (control)
4: silane+hairpin loop probes+gold nanoparticle reporter conjugate (control)

The testing scheme is shown in FIG. 10 the wild-type sequence having a single base mismatch to the probe is shown to be unable to open an hybridize with the hairpin loop probe. However, the perfectly complementary sequence opens the hairpin loop structure. The results were analyzed using 7 base hybridization detection sequence (TGC CTT T) conjugated with a gold nanoparticle (nanoparticle reporter conjugate), where the nanoparticle reporter conjugate hybridizes to the stem region of the opened hairpin loop probe sequence.

The electrodes for each system were probed with an Agilent 4155C semiconductor parameter analyzer with a sweep of −1 to +1 V. The results are shown in FIG. 11.

The nanoparticle reporter conjugates were used as transduction agents and have the capability to enhance the electrical signal many folds compared to change in current caused by DNA hybridization or mDNA formation, thus enhancing the sensitivity of the device. The device is an improvement over prior art devices because it is independent of the target size and there is no need for labeling or modifying the probe or the target.

The probe sequence at surface formed a strong secondary structure of a hairpin loop with a stem size of 6 base pairs having a $\Delta G$ of −4.42 Kcal mole$^{-1}$ at 25° C. SEQ ID NO:2 is the 18 base long sequence that was perfectly complementary to the free end of the probe molecule with a $\Delta G$ of −24.45 Kcal mole$^{-1}$ at 25° C. SEQ ID NO:3, which is the wild-type DNA, is the 18 base long sequence identical to SEQ ID NO:2 except for one mismatch and having a $\Delta G$ of −21.20 Kcal mole$^{-1}$ at 25° C. Nanoparticle reporter conjugates contains the 7 base long hybridization detection sequence (TGC-CTTT), which is designed to bind the stem-forming part of the opened hairpin loop probe sequence only. The nanoparticle reporter conjugate is an important building block in the devices, systems, and methods of the invention because it alleviates the need for tagging the probe or target molecules.

For electrical measures, the hairpin loop probe was immobilized on the silicon surface between the gold electrodes using the surface chemistry described by the techniques described in M. Manning, S. Harvey, P. Galvin, and G. V, *Materials Science and Engineering*, C 23, Volume 23, Issue 3, 347-351 (2003), incorporated herein by reference. After the probe immobilization, the substrates were immersed in a solution containing target molecules at a concentration of 2 fmol/µl in TE buffer at pH 7.4 for 24 hours at 40° C. followed by rinsing with methanol and deionized water. Following this, the gold nanoparticle reporter conjugates were flowed into the device. The gold nanoparticle reporter conjugates bound to the stem forming region of the probe towards the chip surface, a region that only became available when a perfectly complementary target hybridized with the probe.

The same experiment was carried out on bare <100>-oriented p-type silicon wafer diced into small chips. Thermal dry oxidation was carried out to grow 3000 Å silicon dioxide. The diced chips were cleaned in an oxygen plasma barrel etcher at 200 W in Ar+$O_2$.

As described above, four different chips were prepared, including two control chips:
  Control 1: Chip with probe DNA but not exposed to any target DNA
  Control 2: Chip with no probe DNA and not exposed to any target DNA (but with silane SAM surface chemistry).
These control chips were prepared to understand the attachment due to the surface charges and van der Waals forces contributing to background noise and capability of flow-in sequence to open the hairpin probe in the absence of target sequence.

The gold nanoparticle reporter conjugates on the surface of the controls, mismatch target and perfectly complementary target exposed bare silicon chips were visualized using scanning electron microscopy (SEM) and manually counting using ImageJ software (National Institutes of Health, http://rsb.info.nih.gov/ij/). The micrographs are shown in FIGS. 8A to 8C.

Figure 8A:
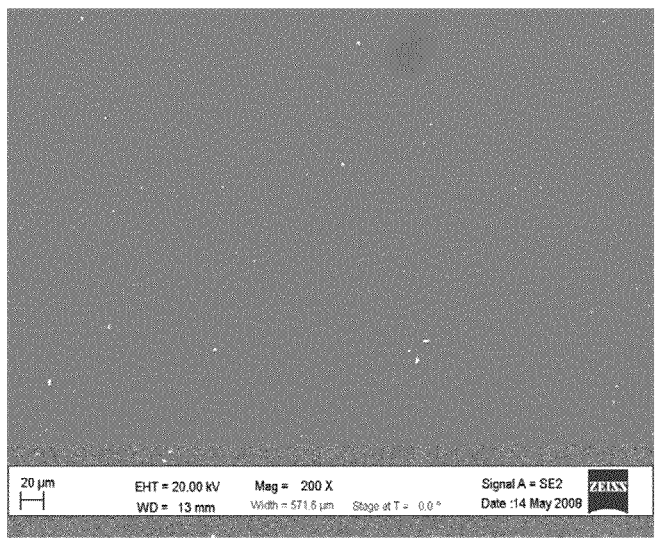
FIGS. 8A, 8B, and 8C show scanning electron micrographs of a silicon dioxide chip with hairpin loop probes at magnifications of 200×, 200×, and 3000×, respectively, where the gold nanoparticle reporter conjugates are shown as white dots.
Figure 8B:
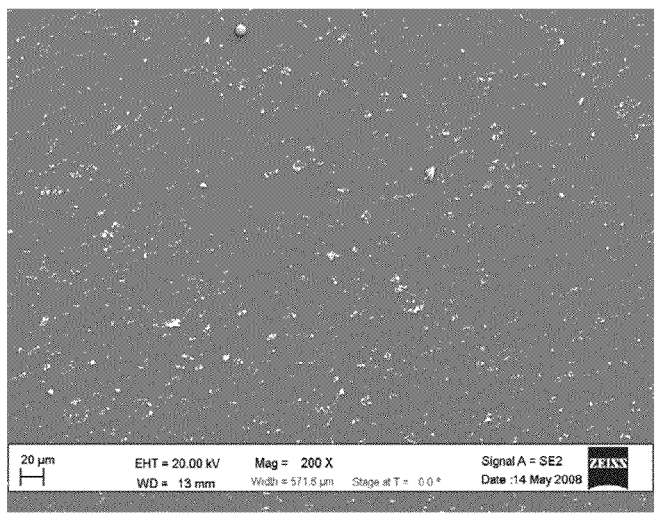
Figure 8C:
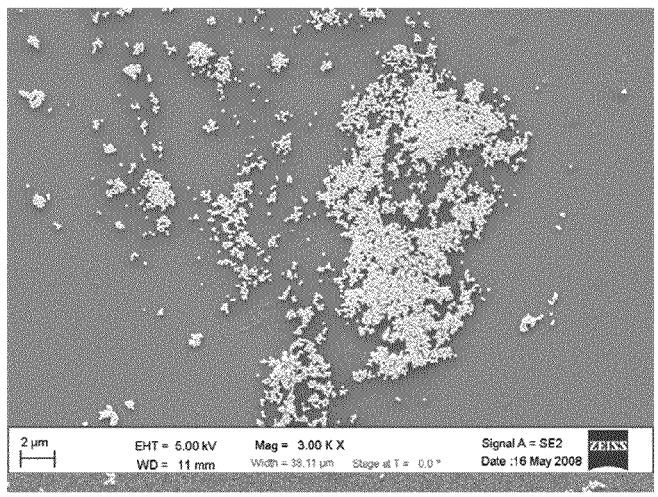

FIGS. 8A, 8B, and 8C show scanning electron micrographs of a silicon dioxide chip with hairpin loop probes at magnifications of 200×, 200×, and 3000×, respectively, where the gold nanoparticle reporter conjugates are shown as white dots. FIG. 8A shows when the device of the invention is exposed to mismatched target for the hairpin loop probes. FIG. 8B shows when the device of the invention is exposed to perfectly complementary target. FIG. 8C shows the details of FIG. 8B. The control chips showed a negligible number of gold nanoparticle reporter conjugates on the surfaces. The chip exposed to the perfectly complementary target showed three orders of magnitude more gold nanoparticle reporter conjugates on the surface compared to the single mismatch target. The few gold nanoparticle reporter conjugates on the mismatched chips can be attributed to physical adsorption.

The number of attached gold nanoparticle reporter conjugates were normalized as count/μm² as shown in Table 2:

TABLE 2

| Chip | Mean number of Particles/μm² | Standard Deviation |
|---|---|---|
| silane + gold nanoparticle reporter conjugate (control) | 0.01 | 0.00 |
| silane + hairpin loop probes + perfectly complementary target + gold nanoparticle reporter conjugate (PC) | 11.62 | 5.60 |
| silane + hairpin loop probes + single base mismatched target + gold nanoparticle reporter conjugate (MM) | 0.86 | 0.76 |
| silane + hairpin loop probes + gold nanoparticle reporter conjugate (control) | 0.10 | 0.09 |

Figure 9:
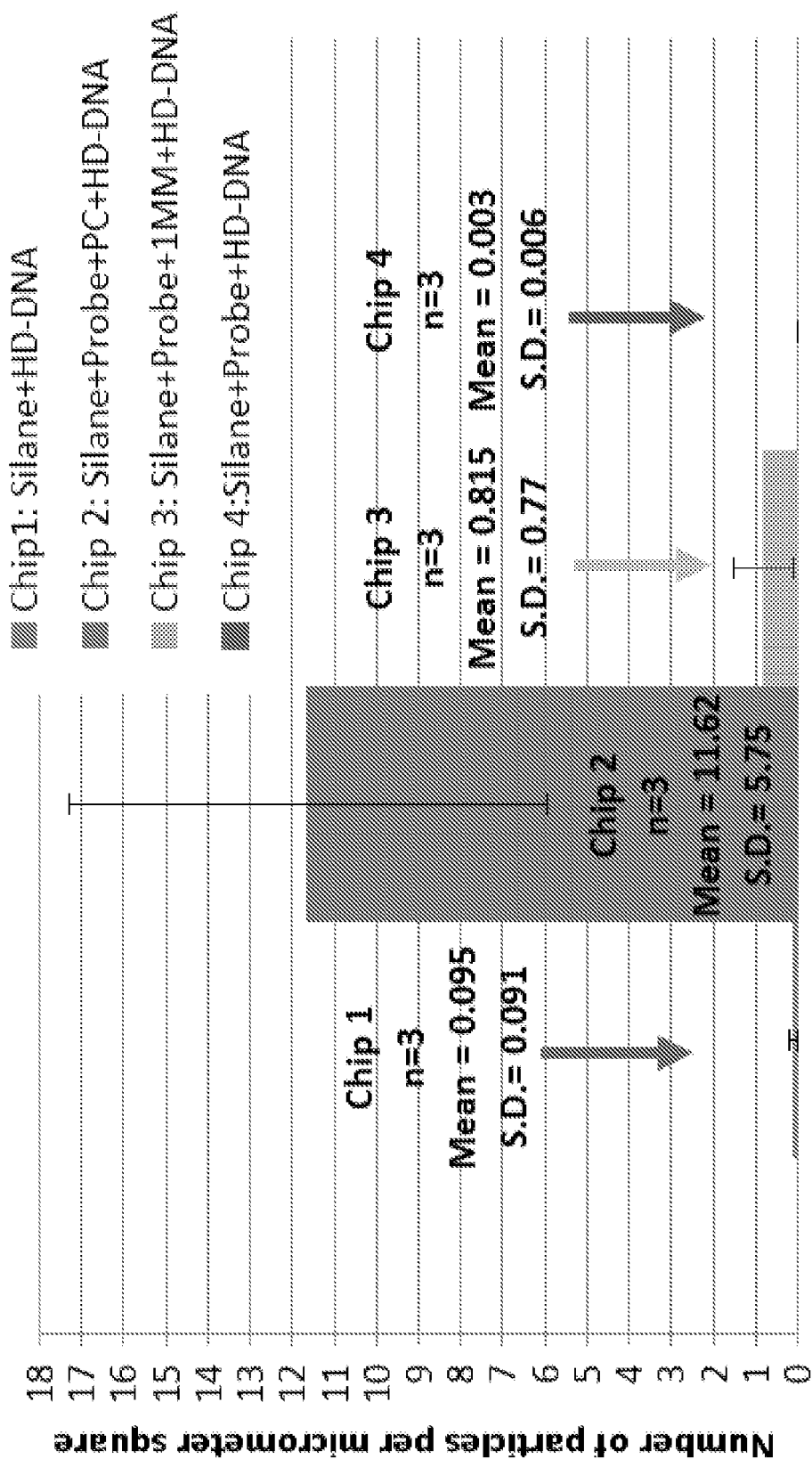
FIG. 9 is a bar graph of the number of nanoparticles per square micrometer for four different scenarios.

A bar graph of the data is shown in FIG. 9.

Current-voltage measurements were made. The data is plotted and shown in FIG. 12 where:

$R_{Before\ DNA} = 50\ G\Omega$ $R_{After\ DNA} = 2.5\ M\Omega$

The current-voltage (I-V) measurements on the MM chips showed a slight increase in conductivity within the same order in 3% of the electrode pairs with the nanogap. On the other hand, more than 70% of the electrode pairs with the nanogap showed a robust increase in conductivity on the PC-exposed chips. There were three orders of reduction in the resistance between the electrodes with the nanogaps for PC-DNA and amplified by the gold nanoparticle reporter conjugate. The presence of the gold nanoparticle reporter conjugates provided charge-hopping sites to carriers, thus acting as a transduction block for the binding of PC with the probe.

FIG. 13A is a scanning electron micrograph of the nanogap prior to hybridization between the oligonucleotide target and the perfectly complementary oligonucleotide hairpin loop probe. FIG. 13B is a scanning electron micrograph of the nanogap after to hybridization between the oligonucleotide target (concentration of 2 fmol/μl) and the perfectly complementary oligonucleotide hairpin loop probe. As can be noted, there is a large population of gold nanoparticle reporter conjugates apparent in the nanogap of FIG. 13B.

The tunneling current in a system with nanogap electrodes with insulator vacuum between them can be approximated by the Simmons formula:

$$J = \frac{\alpha}{\delta_z^2}\{\bar{\varphi}\exp(-A\delta_z\sqrt{\bar{\varphi}}) - (\bar{\varphi}+eV)\exp[-A\delta_z\sqrt{\bar{\varphi}+eV}]\}$$

where $$\alpha = \frac{e}{4\pi^2\beta^2\hbar},\ A = 2\beta\sqrt{\frac{2m}{\hbar^2}},$$

$\bar{\varphi}$ is average barrier height relative to Fermi level of the negative electrode, $\delta_z$ is barrier width and eV is applied bias energy (voltage) between the electrodes. The term β is dimensionless correction factor, e and m are charge and mass of electron respectively, and ℏ is Dirac's constant. At small voltages when $\bar{\varphi} \ll eV$, the Simmons formula simplifies as $$J = \frac{\gamma\sqrt{\bar{\varphi}}V}{\delta_z}\exp(-A\delta_z\sqrt{\bar{\varphi}}),$$

where $$\gamma = \frac{e\sqrt{2m}}{4\beta\pi^2\hbar^2}.$$

In this case $\bar{\varphi}$ does not depend on the applied voltage V between the electrodes so the tunneling current becomes proportional only to V. Thus, in the case of small voltages, the barrier height becomes independent of the applied voltage and the tunneling current becomes linearly dependent only on the applied voltage (See John G. Simmons, *J. Appl. Phys.*, 34, 1793 (1963). The tunneling current characteristics can thus be modeled as two electrodes with high resistance between them. As the PC-target binds between these electrodes and the gold nanoparticle reporter conjugate brings in gold nanoparticles, electrons find a lower barrier and thus start tunneling efficiently.

In summary, the DNA-of-interest target molecules can be electrically detected using engineered hairpin loop probes. The detection of hybridization events can be amplified using a gold nanoparticle reporter conjugate sequence complementary to the stem region of the hairpin loop probe. The presence of the gold nanoparticle between the electrodes enhances the conductivity between otherwise insulated electrodes with a nanogap. The gold nanoparticle reporter conjugates can be modeled as a circuit breaker demonstrating electrical quantification of the molecular interactions. Thus, microarrays of electrodes based on this model are useful in the detection of single base mutations.

The use of the gold-nanoparticles conjugated to a hybridization detection sequence that is capable of binding the stem of region of the opened hairpin loop probe hybridized with only the perfectly complementary target but not with the single base mismatched target demonstrates the ability of the device to detect single base mutations, such as in the k-ras oncogene. Since the k-ras mutation is considered a prognostic indicator for lung cancer patients (M. Huncharek, J. Muscat, and J-F Geschwind, *Carcinogenesis*, 20(8), 1507-1510 (1999)), this device, system, and technique have important diagnostic uses. Of the diseases caused by single nucleotide mutation, k-ras mutation in lung adenocarcinoma is a leading cause of cancer in both men and women in the U.S. The early detection of this mutation can help in timely therapeutics, as the k-ras mutation is thought to be associated with double the risk of death within two years. Similar probes can be designed for genes for other cancers like those for ovarian and breast cancer as well as manner of diseases and conditions associated with gene mutations, especially single base mutations.

Example 3

Materials

Chemicals used in this example were purchased from Sigma-Aldrich (St. Louis, Mo.), except that the 3-amino modified DNA strands were purchased from Alpha DNA (Montreal, Quebec). The DNA binding domain from the *Bombyx mori* retrotransposon protein R2Bm was made in accordance with S. M. Christensen, A. Bibilio, and T. H. Eickbush, *Nucl. Acids Res.* 33:6461-6468 (2005). The zinc finger and myb motif of the R2Bm protein binds to a specific double stranded DNA sequence (5'-CTTAAGGTAGCAAAT-GCCTCGTC-3'; SEQ ID NO:4) with the gene coding for the large ribosomal subunit.

Method

Fabrication of the CMOS Chip: Chips were fabricated in two steps of lithography. On the first layers Ti/Au (thickness 50 Å/150 Å) metal pads 500 nm apart were made using e-beam lithography. Metal lift-off resulted in well-defined structures. In the second step, optical lithography was used to fabricate probing pads to contact the thin film electrodes.

Surface modification and attachment of double-stranded DNA: The silicon chip was cleaned using ultraviolet ozone plasma system. This also resulted in hydrophilic silicon dioxide surface. The attachment chemistry was performed in a nitrogen glovebox in a controlled environment. The chips were silanized in a 3% 3'-aminopropyltrimethoxysilane (APTMS) solution (made with 19:1 methanol-deionized water solution) for over 12 hours. The chips were then cured at 110° C. for 15 minutes. These were then immediately immersed in a N,N-dimethylformamide (DMF) solution containing 10% pyridine and 1 mM 1,4-phenylene diisothiocyanate (PDITC) overnight. After this, the chips were sequentially washed with DMF and 1,2-dichloroethane and dried under nitrogen gas. The double-stranded sequence solution was prepared at a concentration of 1 pmole/μl and chips were immersed in it immediately. The chips were incubated at 37° C. overnight in order to facilitate the covalent attachment of the 3'-amino modified double-stranded DNA with the PDIT crosslinker molecules. The chips were again washed with deionized water, methanol, and dried under nitrogen. The unbound reactive groups from PDITC were deactivated by immersing the chips in a solution of 50 mM 6-amino-1-hexanol and 150 mM DPEA in DMF for 24 hours. The chips were then washed with DMF, acetone, deionized and dried with nitrogen gas.

To confirm the surface modification, energy dispersive x-ray spectroscopy (EDAX), contact angle, and ellipsometry measurements were carried out at every step. The presence of double-stranded DNA immobilized on the silicon surface was confirmed by fluorescence measurements of Acridine Orange stain at 525 nm wavelength using a Zeiss confocal microscope.

Binding between protein and DNA: The double-stranded DNA used in this example was a 23 base-pair fragment of the ribosome gene that corresponds to the binding site of the R2Bm polypeptide. To confirm that the purified R2Bm polypeptide is capable of binding to the short double-stranded DNA, electrophoretic mobility shift assays were run.

Chips with covalently attached double-stranded DNA were then incubated with 2.8 fmol/μl of R2Bm polypeptide for 30 minutes in binding buffer (50 mM Tris-HCl pH 8.0, 100 mM NaCl, 5 mM $MgCl_2$). The presence of the protein on the chip was initially confirmed by optical detection of fluorescent Sypro Ruby Protein Blot stain at 488 nm wavelength. The fluorescence intensity analysis was done by ImageJ software. The presence of protein bound to the double-stranded DNA was also detected electrically by direct current electrical measurements.

Results

The EDAX analysis was used to identify the elemental composition of the silicon surface as the different modifications were added. The data in the table below show the elemental increase in carbon and nitrogen after the double-stranded DNA immobilization:

|  | C | N | O |
|---|---|---|---|
| Clean Chip | 0.2 | 8.2 | 320.4 |
| PDITC | 7.3 | 9.1 | 329.2 |
| DNA | 10.7 | 25.8 | 391.4 |

Control chips without double-stranded DNA showed no change in carbon and nitrogen.

The contact angle measurements showed the silicon surface becoming hydrophilic after plasma treatment and later less hydrophilic when functionalized with APTMS and PDITC. This showed that the surface of silicon chip after plasma etching. Functionalization with APTMS/PDITC reduced available hydroxyl groups on the surface and thus showed reduced hydrophilicity. This also proved that the OH bonds were used up in effective covalent attachment of silane.

The ellipsometry measurements gave the thickness of the self-assembled monolayer (SAM) of silane modification. The I-V data showed a linear trend indicating conducting behavior of the protein. The control chip showed open circuit behavior before and after the functionalization. The resistances of the devices after protein capture ranged from a few ohms to gigaohms, indicating a varying number of proteins bridging the gap between the electrodes.

When ranges are used herein for physical properties, such as molecular weight, or chemical properties, such as chemical formulae, all combinations, and subcombinations of ranges specific embodiments therein are intended to be included.

The disclosures of each patent, patent application and publication cited or described in this document are hereby incorporated herein by reference, in its entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A device, comprising:
   a thermally responsive, electrically insulating substrate;
   at least one heating element; and
   a first detecting unit, comprising:
      a first electrode and a second electrode separated by a nanogap; and
      a plurality of first oligonucleotide probes attached to said substrate in said nanogap;
   wherein said first oligonucleotide probes are in a hairpin loop formation and have the same nucleic acid sequence; and
   wherein said first oligonucleotide probes comprise an optional spacer, a loop, and a stem region, said stem region being double-stranded.

2. A device of claim 1,
   wherein said first oligonucleotide probes form a self-assembled monolayer.

3. A device of claim 1,
wherein said thermally responsive, electrically insulating substrate is silicon, silicon dioxide, or a combination thereof.

4. A device of claim 1, further comprising:
a plurality of additional heating elements capable of forming a temperature gradient.

5. A device of claim 1,
wherein said heating element is embedded in said substrate.

6. A device of claim 1,
wherein said heating element comprises gold.

7. A device of claim 1,
wherein said first detecting unit is located on the surface of said substrate.

8. A device of claim 1,
wherein said first and second electrodes comprise a metal selected from the group consisting of gold, silver, titanium, copper, or a combination thereof.

9. A device of claim 1,
wherein said nanogap is formed by electromigration.

10. A device of claim 1,
wherein said nanogap is about 10 nm to about 500 nm.

11. A device of claim 1,
wherein said first oligonucleotide probes are covalently attached to said substrate.

12. A device of claim 1,
wherein each of said first oligonucleotide probes comprise:
    an optional spacer having about one nucleotide base to about 20 nucleotide bases;
    a nucleotide loop having about 3 nucleotide bases to about 100 nucleotide bases; and
    a base pair stem having about 3 nucleotide base pairs to about 20 nucleotide base pairs.

13. A device of claim 1,
wherein each of said first oligonucleotide probes comprise:
    a spacer having about 3 nucleotide bases;
    a nucleotide loop having about 12 nucleotide bases; and
    a base pair stem having about 6 nucleotide base pairs.

14. A device of claim 1, further comprising:
a plurality of second detecting units, comprising:
    a first electrode and a second electrode separated by a nanogap; and
    a plurality of second oligonucleotide probes attached to said substrate in said nanogap;
    wherein said second oligonucleotide probes are in a hairpin loop formation and have the same nucleic acid sequence;
    wherein said second oligonucleotide probes comprise an optional spacer, a loop, and a stem region, said stem region being double-stranded;
    wherein said second oligonucleotide probes are the same or different from said first oligonucleotide probes in said first detecting unit; and
    wherein said second oligonucleotide probes are the same or different from other second oligonucleotide probes in said plurality of second detecting units.

15. A device of claim 1, further comprising:
a plurality of microfluidic channels; and
an optional cover.

16. A device of claim 1,
wherein said at least one heating element is located in a first layer; and
wherein said first electrode and said second electrodes are located in a second layer.

17. A system, comprising:
a device of claim 1; and
a plurality of nanoparticle reporter conjugates;
wherein said nanoparticle reporter conjugates comprise at least one nanoparticle and a single-stranded oligonucleotide complementary to at least a portion of said stem of said first oligonucleotide probe; and
wherein said nanoparticle is a metal, semiconductor, or magnetic colloidal particle.

18. A system of claim 17,
wherein said single-stranded oligonucleotide complementary to at least a portion of said stem of said first oligonucleotide probe comprises about 3 nucleotide bases to about 80 nucleotide bases.

19. A system of claim 17,
wherein said single-stranded oligonucleotide complementary to at least a portion of said stem of said first oligonucleotide probe comprises about 7 nucleotide bases.

20. A system, comprising:
a device of claim 14; and
a plurality of first nanoparticle reporter conjugates; and
a plurality of at least one second nanoparticle reporter conjugates;
wherein said first nanoparticle reporter conjugates comprise at least one nanoparticle and a single-stranded oligonucleotide complementary to at least a portion of said stem of said first oligonucleotide probes;
wherein said nanoparticle in said first nanoparticle reporter conjugate is a metal, semiconductor, or magnetic colloidal particle;
wherein said second nanoparticle reporter conjugates comprise at least one nanoparticle and a single-stranded oligonucleotide complementary to at least a portion of said stem of said second oligonucleotide probes;
wherein said nanoparticle in said second nanoparticle reporter conjugate is a metal, semiconductor, or magnetic colloidal particle;
wherein said second nanoparticle reporter conjugates are the same or different from said first nanoparticle reporter conjugates; and
wherein said second nanoparticle reporter conjugates are the same or different from said other second nanoparticle reporter conjugates.

21. A system of claim 20,
wherein said single-stranded oligonucleotide complementary to at least a portion of said stem of said hairpin loop probe comprises about 3 nucleotide bases to about 80 nucleotide bases.

22. A system of claim 20,
wherein said single-stranded oligonucleotide complementary to at least a portion of said stem of said hairpin loop probe comprises about 7 nucleotide bases.

23. A system of claim 17 or 20, further comprising:
an electrical reading device for interrogating said device of claim 1.

24. A system of claim 23,
wherein said electrical reading device is portable.

25. A method for detecting nucleic acid hybridization, comprising:
providing a device, comprising:
    a thermally responsive, electrically insulating substrate;
    at least one heating element; and
    a first detecting unit, comprising:
        a first electrode and a second electrode separated by a nanogap; and
        a plurality of first oligonucleotide probes attached to said substrate in said nanogap;

wherein said first oligonucleotide probes are in a hairpin loop formation and have the same nucleic acid sequence; and wherein said first oligonucleotide probes comprise an optional spacer, a loop, and a stem region, said stem region being double-stranded;

providing a solution comprising at least one buffer and single-stranded oligonucleotide target under hybridizing conditions;

wherein said single-stranded oligonucleotide target hybridizes at least some of said first oligonucleotide probes to form elongated oligonucleotide probes;

providing a plurality of first nanoparticle reporter conjugates under hybridizing conditions;

wherein said first nanoparticle reporter conjugates comprise at least one nanoparticle and an oligonucleotide complementary to at least a portion of said stem of said first oligonucleotide probes;

wherein said nanoparticle in said first nanoparticle reporter conjugate is a metal, semiconductor, or magnetic colloidal particle;

applying a voltage drop across said electrodes; and measuring a change in conductivity, resistivity, capacitance, or impedance across said electrodes at known locations to determine perfect complementarity of said oligonucleotide target to said first oligonucleotide probes.

26. A method of claim 25,
wherein said voltage drop is applied as direct current.
27. A method of claim 25,
wherein said voltage drop is applied as alternating current.
28. A method of claim 25,
wherein said measuring step measures an increase in conductivity across said electrodes at known locations to determine perfect complementarity of said oligonucleotide target to said first oligonucleotide probes.
29. A method of claim 25,
wherein said single-stranded oligonucleotide target is prepared by heating a solution comprising double-stranded oligonucleotide target.
30. A method of claim 25, further comprising:
washing to remove unhybridized components from said detecting unit.
31. A method of claim 25, further comprising:
heating said device to remove said hybridized targets and said hybridized nanoparticle reporter conjugates from said probe to permit recycling of said detecting unit.
32. A method of claim 25, further comprising:
heating a solution comprising double stranded oligonucleotide target to form said solution comprising single-stranded oligonucleotide target.
33. A method of claim 25, further comprising:
forming a temperature gradient to focus said single stranded oligonucleotide target at said detecting unit.
34. A method of claim 25, further comprising:
reversing the polarity of said voltage drop to remove unbound components or nonspecifically bound components from said detecting unit.
35. A method of claim 25, further comprising:
providing, in addition to said first detecting unit, a plurality of additional detecting units, each additional detecting unit comprising:
a first electrode and a second electrode separated by a nanogap; and
a plurality of second oligonucleotide probes attached to said substrate in said nanogap;

wherein said second oligonucleotide probes are in a hairpin loop formation and have the same nucleic acid sequence; and wherein said second oligonucleotide probes comprise an optional spacer, a loop, and a stem region, said stem region being double-stranded wherein said second oligonucleotide probes are the same or different from said first oligonucleotides in said first detecting unit; and wherein said second oligonucleotide probes are the same or different from other second oligonucleotide probes in said plurality of second detecting units;

providing a plurality of at least one second nanoparticle reporter conjugates under hybridizing conditions;

wherein said second nanoparticle reporter conjugates comprise at least one nanoparticle and an oligonucleotide complementary to at least a portion of said stem of said second oligonucleotide probes;

wherein said nanoparticle in said second nanoparticle reporter conjugate is a metal, semiconductor, or magnetic colloidal particle;

wherein said second nanoparticle reporter conjugates are the same or different from said first nanoparticle reporter conjugates;

wherein said second nanoparticle reporter conjugates are the same or different from said other second nanoparticle reporter conjugates;

wherein said measuring step is carried out in parallel or sequentially for said first detecting unit and said plurality of said additional detecting units.

36. A method for detecting nucleic acid hybridization, comprising:
providing a device, comprising:
a thermally responsive, electrically insulating substrate;
at least one heating element; and
a first detecting unit, comprising:
a first electrode and a second electrode separated by a nanogap; and
a plurality of first oligonucleotide probes attached to said substrate in said nanogap;
wherein said first oligonucleotide probes are in a hairpin loop formation and have the same nucleic acid sequence; and
wherein said first oligonucleotide probes comprise an optional spacer, a loop, and a stem region, said stem region being double-stranded;
providing a solution comprising at least one buffer and single-stranded oligonucleotide target under hybridizing conditions;
wherein said single-stranded oligonucleotide target hybridizes at least some of said first oligonucleotide probes to form elongated oligonucleotide probes;
providing a plurality of first reporter conjugates under hybridizing conditions;
wherein said first reporter conjugates comprise an oligonucleotide complementary to at least a portion of said stem of said first oligonucleotide probes;
reversibly exchanging an imino proton in each base pair of said first reporter conjugate or said stem of said first oligonucleotide probes with a metal ion selected from the group consisting of gold ion, silver ion, platinum ion, and copper ion;
applying a voltage drop across said electrodes; and
measuring a change in conductivity, resistivity, capacitance, or impedance across said electrodes at known locations to determine perfect complementarity of said oligonucleotide target to said first oligonucleotide probes.

37. A method of claim 36, further comprising:
providing, in addition to said first detecting unit, a plurality of additional detecting units, each additional detecting unit comprising:
  a first electrode and a second electrode separated by a nanogap; and
  a plurality of second oligonucleotide probes attached to said substrate in said nanogap;
  wherein said second oligonucleotide probes are in a hairpin loop formation and have the same nucleic acid sequence; and
  wherein said second oligonucleotide probes comprise an optional spacer, a loop, and a stem region, said stem region being double-stranded;
  wherein said second oligonucleotide probes are the same or different from said first oligonucleotides in said first detecting unit; and
  wherein said second oligonucleotide probes are the same or different from other second oligonucleotide probes in said plurality of second detecting units;
providing a plurality of at least one second reporter conjugates under hybridizing conditions;
  wherein said second reporter conjugates comprise an oligonucleotide complementary to at least a portion of said stem of said second oligonucleotide probes;
  wherein said second reporter conjugates are the same or different from said first nanoparticle reporter conjugates;
  wherein said second reporter conjugates are the same or different from said other second nanoparticle reporter conjugates;
reversibly exchanging an imino proton in each base pair of said second reporter conjugate or said stem of said second oligonucleotide probes with a metal ion selected from the group consisting of gold ion, silver ion, platinum ion, and copper ion;
wherein said measuring step is carried out in parallel or sequentially for said first detecting unit and said plurality of said additional detecting units.

38. A method for detecting nucleic acid hybridization, comprising:
providing a device, comprising:
  a thermally responsive, electrically insulating substrate;
  at least one heating element; and
  a first detecting unit, comprising:
    a first electrode and a second electrode separated by a nanogap; and
    a plurality of first oligonucleotide probes attached to said substrate in said nanogap;
    wherein said first oligonucleotide probes are in a hairpin loop formation and have the same nucleic acid sequence; and
    wherein said first oligonucleotide probes comprise an optional spacer, a loop, and a stem region, said stem region being double-stranded;
providing a solution comprising at least one buffer and single-stranded oligonucleotide target under hybridizing conditions;
  wherein said single-stranded oligonucleotide target hybridizes at least some of said first oligonucleotide probes to form elongated oligonucleotide probes;
providing a plurality of first nanoparticle reporter conjugates under hybridizing conditions to form a double stranded nucleic acid sequence;
  wherein said first nanoparticle reporter conjugates comprise an oligonucleotide complementary to at least a portion of said stem of said first oligonucleotide probes;
vectorially depositing silver on said double stranded nucleic acid sequence;
applying a voltage drop across said electrodes; and
measuring a change in conductivity, resistivity, capacitance, or impedance across said electrodes at known locations to determine perfect complementarity of said oligonucleotide target to said first oligonucleotide probes.

39. A method of claim 38,
wherein said vectorially depositing step comprises:
ion exchanging silver ions on said double stranded nucleic acid sequence;
reducing said silver ions; and
developing silver aggregates on said double stranded nucleic acid sequence.

40. A method of claim 38, further comprising:
providing, in addition to said first detecting unit, a plurality of additional detecting units, each additional detecting unit comprising:
  a first electrode and a second electrode separated by a nanogap; and
  a plurality of second oligonucleotide probes attached to said substrate in said nanogap;
  wherein said second oligonucleotide probes are in a hairpin loop formation and have the same nucleic acid sequence;
  wherein said second oligonucleotide probes comprise an optional spacer, a loop, and a stem region, said stem region being double-stranded;
  wherein said second oligonucleotide probes are the same or different from said first oligonucleotides in said first detecting unit; and
  wherein said second oligonucleotide probes are the same or different from other second oligonucleotide probes in said plurality of second detecting units;
providing a plurality of at least one second reporter conjugates under hybridizing conditions;
  wherein said second reporter conjugates comprise an oligonucleotide complementary to at least a portion of said stem of said second oligonucleotide probes;
  wherein said second reporter conjugates are the same or different from said first nanoparticle reporter conjugates;
  wherein said second reporter conjugates are the same or different from said other second nanoparticle reporter conjugates; and
vectorially depositing silver on said double stranded nucleic acid sequence;
wherein said measuring step is carried out in parallel or sequentially for said first detecting unit and said plurality of said additional detecting units.

41. A method for detecting nucleic acid hybridization, comprising:
providing a device, comprising:
  a thermally responsive, electrically insulating substrate;
  at least one heating element; and
  a first detecting unit, comprising:
    a first electrode and a second electrode separated by a nanogap; and
    a plurality of first oligonucleotide probes attached to said substrate in said nanogap;

wherein said first oligonucleotide probes are in a hairpin loop formation and have the same nucleic acid sequence; and wherein said first oligonucleotide probes comprise an optional spacer, a loop, and a stem region, said stem region being double-stranded;

providing a solution comprising at least one buffer and single-stranded oligonucleotide target under hybridizing conditions;

wherein said single-stranded oligonucleotide target hybridizes at least some of said first oligonucleotide probes to form elongated oligonucleotide probes;

providing a plurality of first reporter molecules under hybridizing conditions to form a double stranded oligonucleotide-stem complex;

wherein said first reporter molecules comprise an oligonucleotide complementary to at least a portion of said stem of said first oligonucleotide probes;

providing a solution comprising first nanoparticle polypeptide conjugates;

wherein said first nanoparticle polypeptide conjugates comprise at least one nanoparticle and a polypeptide that binds to said double stranded oligonucleotide-stem complex;

wherein said nanoparticle in said first nanoparticle polypeptide conjugates is a metal, semiconductor, or magnetic colloidal particle;

applying a voltage drop across said electrodes; and measuring a change in conductivity, resistivity, capacitance, or impedance across said electrodes at known locations to determine perfect complementarity of said oligonucleotide target to said first oligonucleotide probes.

42. A method of claim 41, further comprising:

providing, in addition to said first detecting unit, a plurality of additional detecting units, each additional detecting unit comprising:

a first electrode and a second electrode separated by a nanogap; and a plurality of second oligonucleotide probes attached to said substrate in said nanogap;

wherein said second oligonucleotide probes are in a hairpin loop formation and have the same nucleic acid sequence;

wherein said second oligonucleotide probes comprise an optional spacer, a loop, and a stem region, said stem region being double-stranded;

wherein said second oligonucleotide probes are the same or different from said first oligonucleotides in said first detecting unit; and wherein said second oligonucleotide probes are the same or different from other second oligonucleotide probes in said plurality of second detecting units;

providing a plurality of second reporter molecules under hybridizing conditions to form a double stranded oligonucleotide-stem complex;

wherein said second reporter molecules comprise an oligonucleotide complementary to at least a portion of said stem of said second oligonucleotide probes;

providing a solution comprising second nanoparticle polypeptide conjugates;

wherein said second nanoparticle polypeptide conjugates comprise at least one nanoparticle and a polypeptide that binds to said double stranded oligonucleotide-stem complex;

wherein said nanoparticle in said second nanoparticle polypeptide conjugates is a metal, semiconductor, or magnetic colloidal particle;

wherein said second reporter molecules are the same or different from said first reporter molecules;

wherein said second reporter molecules are the same or different from other second reporter molecules;

wherein said measuring step is carried out in parallel or sequentially for said first detecting unit and said plurality of said additional detecting units.

* * * * *

UNITED STATES PATENT AND TRADEMARK OFFICE
CERTIFICATE OF CORRECTION

PATENT NO. : 8,283,936 B2
APPLICATION NO. : 12/701888
DATED : October 9, 2012
INVENTOR(S) : Samir M. Iqbal et al.

It is certified that error appears in the above-identified patent and that said Letters Patent is hereby corrected as shown below:

In the Specification

Column 1, lines 10-15 should read,

--In the "REFERENCE TO GOVERNMENT GRANTS" the existing paragraph should be replaced with: "This invention was made with government support under grant/contract number ECCS 0845669 awarded by the National Science Foundation. The government has certain rights in the invention."--

Signed and Sealed this
Fourteenth Day of October, 2014

Michelle K. Lee
*Deputy Director of the United States Patent and Trademark Office*

SEQUENCE LISTING

<160> NUMBER OF SEQ ID NOS: 5

<210> SEQ ID NO 1
<211> LENGTH: 27
<212> TYPE: DNA
<213> ORGANISM: artificial
<220> FEATURE:
<223> OTHER INFORMATION: Artificial = synthetic construct
<220> FEATURE:
<221> NAME/KEY: modified_base
<222> LOCATION: (1)..(1)
<223> OTHER INFORMATION: C12 amine

<400> SEQUENCE: 1
aaaggcaatt tcgccgccgc cattgcc                          27

<210> SEQ ID NO 2
<211> LENGTH: 18
<212> TYPE: DNA
<213> ORGANISM: artificial
<220> FEATURE:
<223> OTHER INFORMATION: Artificial = synthetic construct

<400> SEQUENCE: 2
ggcaatggcg gcggcgaa                                    18

<210> SEQ ID NO 3
<211> LENGTH: 18
<212> TYPE: DNA
<213> ORGANISM: artificial
<220> FEATURE:
<223> OTHER INFORMATION: Artificial = synthetic construct

<400> SEQUENCE: 3
ggcagtggcg gcggcgaa                                    18

<210> SEQ ID NO 4
<211> LENGTH: 23
<212> TYPE: DNA
<213> ORGANISM: artificial
<220> FEATURE:
<223> OTHER INFORMATION: Artificial = synthetic construct

<400> SEQUENCE: 4
cttaaggtag caaatgcctc gtc                              23

<210> SEQ ID NO 5
<211> LENGTH: 27
<212> TYPE: DNA
<213> ORGANISM: artificial
<220> FEATURE:
<223> OTHER INFORMATION: Artificial = synthetic construct

<400> SEQUENCE: 5
aaaggcaatt tcgccgccgc cattgcc                          27